(12) United States Patent
Jose et al.

(10) Patent No.: US 9,303,005 B2
(45) Date of Patent: Apr. 5, 2016

(54) USE OF DIBENZOFURANONE DERIVATIVES TO INHIBIT KINASES

(76) Inventors: Joachim Jose, Düsseldorf (DE);
Claudia Götz, Saarbrücken (DE);
Andreas Gratz, Düsseldorf (DE); Uwe Kuckländer, Pulheim (DE)

(*) Notice: Subject to any disclaimer, the term of this patent is extended or adjusted under 35 U.S.C. 154(b) by 0 days.

(21) Appl. No.: 13/806,694

(22) PCT Filed: Jun. 22, 2011

(86) PCT No.: PCT/EP2011/060433
§ 371 (c)(1),
(2), (4) Date: May 7, 2013

(87) PCT Pub. No.: WO2011/161151
PCT Pub. Date: Dec. 29, 2011

(65) Prior Publication Data
US 2013/0225674 A1    Aug. 29, 2013

(30) Foreign Application Priority Data
Jun. 25, 2010 (DE) .......................... 10 2010 025 173

(51) Int. Cl.
| | | |
|---|---|---|
| C07D 307/82 | (2006.01) | |
| A61K 31/343 | (2006.01) | |
| A61K 45/06 | (2006.01) | |
| C07D 307/79 | (2006.01) | |

(52) U.S. Cl.
CPC ............ C07D 307/82 (2013.01); A61K 31/343 (2013.01); A61K 45/06 (2013.01); C07D 307/79 (2013.01)

(58) Field of Classification Search
CPC ... A61K 31/343; A61K 45/06; C07D 307/79; C07D 307/82; C07D 307/91; G02B 5/3025; G02B 5/3083; H01L 51/5262; H01L 51/5281
See application file for complete search history.

(56) References Cited

FOREIGN PATENT DOCUMENTS

| | | |
|---|---|---|
| DE | 10 2010 025 173 | 6/2010 |
| WO | WO 2008/028168 | 3/2008 |
| WO | PCT/EP2011/060433 | 6/2011 |

OTHER PUBLICATIONS

Kuckländer et al. Reaction of 2-(aminomethylene)cyclohexanone derivatives with dichloroquinones, (1983) Chem. Ber. 116, pp. 152-158.*
Kuckländer et al. Reaction of 2-(Aminomethylene)cyclohexanone Derivatives with Dichloroquinones. Chem. Ber. (1983), vol. 116, p. 152-158.*
Lopez-Ramos et al. New potent dual inhibitors of CK2 and Pim kinases: discovery and structural insights. The FASEB Journal (2010) vol. 24, p. 3171-3185.*
Vogelstein et al. Cancer genes and the pathways they control. Nature Medicine (2004), vol. 10, pp. 789-799.*
Prudent et al. New Protein Kinase CK2 Inhibitors: Jumping out of the Catalytic Box. (2009), vol. 16, pp. 112-120.*
Toluene New Jersey Department of Health. 1998 [Retrieved on:Feb. 3, 2014] <url: http://nj.gov/health/eoh/rtkweb/documents/fs/1866.pdf>.*
Ahmad, K.A., et al. (2008) Protein kinase CK2-a key suppressor of apoptosis. Adv Enzyme Regul 48:179-87.
Ahmed, K., et al. (1994) Editorial. Cell Mol Biol Res 40:371-2.
Allende, J.E. and Allende, C.C. (1995) Protein kinase CK2: an enzyme with multiple substrates and a puzzling regulation. FASEB J 9:313-23.
Allende-Vega, N., et al. (2005) Phosphorylation of the acidic domain of Mdm2 by protein kinase CK2. Mol Cell Biochem 274:85-90.
Augustine, S.A.J., et al. (2006) Molecular cloning of a Trypanosoma cruzi cell surface casein kinase II substrate, Tc-1, involved in cellular infection. Infect Immun 74:3922-9.
Barz, T., et al. (2003) Genome-wide expression screens indicate a global role for protein kinase CK2 in chromatin remodeling. J Cell Sci 116:1563-77.
Battistutta, R. (2009) Protein kinase CK2 in health and disease: Structural bases of protein kinase CK2 inhibition. Cell Mol Life Sci 66:1868-89.
Battistutta, R., et al. (2000) The replacement of ATP by the competitive inhibitor emodin induces conformational modifications in the catalytic site of protein kinase CK2. J Biol Chem 275:29618-22.
Bibby, A.C. and Litchfield, D.W. (2005) The multiple personalities of the regulatory subunit of protein kinase CK2: CK2 dependent and CK2 independent roles reveal a secret identity for CK2beta. Int J Biol Sci 1:67-79.
Blanquet, P.R. (2000) Casein kinase 2 as a potentially important enzyme in the nervous system. Prog Neurobiol 60:211-46.
Blume-Jensen, P. and Hunter, T. (2001) Oncogenic kinase signalling. Nature 411:355-65.
Bollig, R. (2007) Neue cytostatisch wirksame Reaktionsprodukte der erweiterten Nenitzescu-Reaktion. Dissertation, Heinrich-Heine-Universität, Düsseldorf.
Bortolato, A., et al. (2008) Protein kinase CK2 inhibitors: emerging anticancer therapeutic agents? Anti-Cancer Agents Med Chem 8:798-806.
Bretner, M., et al. (2008) New inhibitors of protein kinase CK2, analogues of benzimidazole and benzotriazole. Mol Cell Biochem 316:87-9.
Brown, C.J., et al. (2009) Awakening guardian angels: drugging the p53 pathway. Nat Rev Cancer 9:862-73.
Buchou, T., et al. (2003) Disruption of the regulatory beta subunit of protein kinase CK2 in mice leads to a cell-autonomous defect and early embryonic lethality. Mol Cell Biol 23:908-15.

(Continued)

Primary Examiner — Melenie McCormick
Assistant Examiner — Taina D Matos Negron
(74) Attorney, Agent, or Firm — Ballard Spahr LLP

(57) ABSTRACT

The invention relates to a pharmaceutical product comprising a dibenzofuranone derivative as the active ingredient. The invention further relates to the use of dibenzofuranone derivatives to inhibit kinases, in particular serine/threonine kinases, to the use of dibenzofuranone derivatives for producing drugs and/or medicinal products for treatment, and to the use of dibenzofuranone derivatives as a diagnostic product for analyzing the role of protein kinases, in particular serine/threonine kinases, in particular protein kinase CK2 in cellular processes, the pathogenesis of diseases, ontogenesis and/or other developmental biological phenomena or relationships.

4 Claims, 13 Drawing Sheets

(56) References Cited

OTHER PUBLICATIONS

Burnett, G. and Kennedy, E.P. (1954) The enzymatic phosphorylation of proteins. *J Biol Chem* 211:969-80.
Caples, M.J., et al. (2006) Protein kinase CK2 phosphorylates the Nef protein from a neurovirulent simian immunodeficiency virus. *Virology* 348:156-64.
Carpenter, G., et al. (1979) Rapid enhancement of protein phosphorylation in A-431 cell membrane preparations by epidermal growth factor. *J Biol Chem* 254:4884-91.
Chalhoub, N. and Baker, S.J. (2009) PTEN and the PI3-kinase pathway in cancer. *Annu Rev Pathol* 4:127-50.
Cheek, S., et al. (2005) A comprehensive update of the sequence and structure classification of kinases. *BMC Struct Biol* 5:6.
Cheek, S., et al. (2002) Sequence and structure classification of kinases. *J Mol Biol* 320:855-81.
Chen, J., et al. (2008) Casein kinase II interacts with prion protein in vitro and forms complex with native prion protein in vivo. *Acta Biochim Biophys Sin (Shanghai)* 40:1039-47.
Chien, W.M., et al. (2000) Casein kinase II phosphorylation of the human papillomavirus-18 E7 protein is critical for promoting S-phase entry. *Cell Growth Differ* 11:425-35.
Cohen, P. (1999) The development and therapeutic potential of protein kinase inhibitors. *Curr Opin Chem Biol* 3:459-65.
Cohen, P. (2002a) The origins of protein phosphorylation. *Nat Cell Biol* 4:E127-30.
Cohen, P. (2002b) Protein kinases—the major drug targets of the twenty-first century? *Nat Rev Drug Discov* 1:309-15.
Cozza, G., et al. (2006) Identification of ellagic acid as potent inhibitor of protein kinase CK2: a successful example of a virtual screening application. *J Med Chem* 49:2363-6.
Cozza, G., et al. (2010) How druggable is protein kinase CK2? *Med Res Rev* 30:419-62.
Cozza, G., et al. (2009) Quinalizarin as a potent, selective and cell-permeable inhibitor of protein kinase CK2. *Biochem J* 421:387-95.
Dancey, J.E. (2009) Kinase inhibitor 4 minisymposium summary. *Expert Rev Anticancer Ther* 9:891-4.
Daya-Makin, M., Sanghera, J.S., Mogentale, T.L., Lipp, M., Parchomchuk, J., Hogg, J.C. and Pelech, S.L. (1994) Activation of a tumor-associated protein kinase mase (p40TAK) and casein kinase 2 in human squamous cell carcinomas and adenocarcinomas of the lung. *Cancer Res* 54:2262-8.
Deana, A.D., et al. (1978) Different susceptibility of whole casein components to enzymatic phosphorylation by two forms of rat liver 'casein kinase'. *Biochim Biophys Acta* 524:316-26.
Delorme, V., et al. (2003) Actin dynamics is controlled by a casein kinase II and phosphatase 2C interplay on *Toxoplasma gondii* Toxofilin. *Mol Biol Cell* 14:1900-12.
DePaoli-Roach, A.A., et al. (1981) Phosphorylation of glycogen synthase and of the beta subunit of eukaryotic initiation factor two by a common protein kinase. *J Biol Chem* 256:8871-4.
Desagher, S., et al. (2001) Phosphorylation of bid by casein kinases I and II regulates its cleavage by caspase 8. *Mol Cell* 8:601-11.
Di Maira, et al. (2009) Dephosphorylation and inactivation of Akt/PKB is counteracted by protein kinase CK2 in HEK 293T cells. *Cell Mol Life Sci* 66:3363-73.
Di Maira, G., et al. (2005) Protein kinase CK2 phosphorylates and upregulates Akt/PKB. *Cell Death Differ* 12:668-77.
Dominguez, I., Sonenshein, G.E. and Seldin, D.C. (2009) Protein kinase CK2 in health and disease: CK2 and its role in Wnt and NF-kappaB signaling: linking development and cancer. *Cell Mol Life Sci* 66:1850-7.
Druker, B.J. (2009) Perspectives on the development of imatinib and the future of cancer research. *Nat Med* 15:1149-52.
Eglen, R.M. and Reisine, T. (2009) The current status of drug discovery against the human kinome. *Assay Drug Dev Technol* 7:22-43.
Escalier, D., et al. (2003) Spermatogenesis of mice lacking CK2alpha': failure of germ cell survival and characteristic modifications of the spermatid nucleus. *Mol Reprod Dev* 66:190-201.

Farah, M., et al. (2003) 5,6-Dichloro-ribifuranosylbenzimidazole- and apigenin-induced sensitization of colon cancer cells to TNF-alpha-mediated apoptosis. *Am J Physiol Gastrointest Liver Physiol* 285:G919-28.
Faust, M. and Montenarh, M. (2000) Subcellular localization of protein kinase CK2. A key to its function? *Cell Tissue Res* 301:329-40.
Faust, R.A., et al (1999) Subcellular immunolocalization of protein kinase CK2 in normal and carcinoma cells. *Int J Biochem Cell Biol* 31:941-9.
Filhol, O. and Cochet, C. (2009) Protein kinase CK2 in health and disease: Cellular functions of protein kinase CK2: a dynamic affair. *Cell Mol Life Sci* 66:1830-9.
Fu, L. and Lee, C.C. (2003) The circadian clock: pacemaker and tumour suppressor. *Nat Rev Cancer* 3:350-61.
Glover, C.V. (1998) On the physiological role of casein kinase II in *Saccharomyces cerevisiae*. *Prog Nucleic Acid Res Mol Biol* 59:95-133.
Graham, K.C. and Litchfield, D.W. (2000) The regulatory beta subunit of protein kinase CK2 mediates formation of tetrameric CK2 complexes. *J Biol Chem* 275:5003-10.
Graziani, Y., Erikson, E. and Erikson, R.L. (1983) Characterization of the Rous sarcoma virus transforming gene product. *J Biol Chem* 258:6344-51.
Guerra, B. (2006) Protein kinase CK2 subunits are positive regulators of AKT kinase. *Int J Oncol* 28:685-93.
Guerra, B. and Issinger, O.-G. (1999) Protein kinase CK2 and its role in cellular proliferation, development and pathology. *Electrophoresis* 20:391-408.
Guerra, B. and Issinger, O.-G. (2008) Protein kinase CK2 in human diseases. *Curr Med Chem* 15:1870-86.
Hanahan, D. and Weinberg, R.A. (2000) The hallmarks of cancer. *Cell* 100:57-70.
Harvey, E.J., et al. (2007) Critical role for casein kinase 2 and phosphoinositide-3 kinase in the interferon-gamma-induced expression of monocyte chemoattractant protein-1 and other key genes implicated in atherosclerosis. *Arterioscler Thromb Vasc Biol* 27:806-12.
Hastie, C.J., et al. (2006) Assay of protein kinases using radiolabeled ATP: a protocol. *Nat Protoc* 1:968-71.
Hidaka, H., et al. (1984) Isoquinolinesulfonamides, novel and potent inhibitors of cyclic nucleotide dependent protein kinase and protein kinase C. *Biochemistry*.
Homma, M.K. and Homma, Y. (2008) Cell cycle and activation of CK2. *Mol Cell Biochem* 316:49-55.
Hora, R., et al. (2009) Erythrocytic casein kinase II regulates cytoadherence of *Plasmodium falciparum*-infected red blood cells. *J Biol Chem* 284:6260-9.
Hung, M.-S., et al. (2009) Identification of hematein as a novel inhibitor of protein kinase CK2 from a natural product library. *BMC Canc* 9:135.
Jia, Y., et al. (2008) Current in vitro kinase assay technologies: the quest for a universal format. *Curr Drug Discov Technol* 5:59-69.
Kelliher, M.A., et al. (1996) Tal-1 induces T cell acute lymphoblastic leukemia accelerated by casein kinase II alpha. *EMBO J* 15:5160-6.
Kennedy, E. and Smith, S. (1954) The isolation of radioactive phosphoserine from phosphoprotein of the Ehrlich ascites tumor. *J Biol Chem* 207:153-63.
Kim, J.S., et al. (2007) Protein kinase CK2alpha as an unfavorable prognostic marker and novel therapeutic target in acute myeloid leukemia. *Clin Cancer Res* 13:1019-28.
Klumpp, S. and Krieglstein, J. (2005) Reversible phosphorylation of histidine residues in vertebrate proteins. *Biochim Biophys Acta* 1754:291-5.
Knight, Z.A. and Shokat, K.M. (2005) Features of selective kinase inhibitors. *Chem Biol* 12:621-37.
Kramerov, A.A., et al. (2008) Inhibition of protein kinase CK2 suppresses angiogenesis and hematopoietic stem cell recruitment to retinal neovascularization sites. *Mol Cell Biochem* 316:177-86.
Krebs, E.G. and Fischer, E. (1956) The phosphorylase b to a converting enzyme of rabbit skeletal muscle. *Biochim Biophys Acta* 20:150-7.

(56) References Cited

OTHER PUBLICATIONS

Kuckländer, U. and Töberich, H. (1982) Zur Umsetzung von 2-(Aminomethylen)cyclohexanon-Derivaten with Dichlorchinonen. *Chem Ber* 116:152-8.

Kuenzel, E.A., et al. (1987) Substrate specificity determinants for casein kinase II as deduced from studies with synthetic peptides. *J Biol Chem* 262:9136-40.

Landesman-Bollag, E., et al. (1998) p53 deficiency and misexpression of protein kinase CK2alpha collaborate in the development of thymic lymphomas in mice. *Oncogene* 16:2965-74.

Landesman-Bollag, E., et al. (2001a) Protein kinase CK2 in mammary gland tumorigenesis. *Oncogene* 20:3247-57.

Landesman-Bollag, E., et al. (2001b) Protein kinase CK2: signaling and tumorigenesis in the mammary gland. *Mol Cell Biochem* 227:153-65.

Lane, D.P. (1992) Cancer. p53, guardian of the genome. *Nature* 358:15-6.

Laramas, M., et al. (2007) Nuclear localization of protein kinase CK2 catalytic subunit (CK2alpha) is associated with poor prognostic factors in human prostate cancer. *Eur J Cancer* 43:928-34.

Laudet, B., et al. (2007) Structure-based design of small peptide inhibitors of protein kinase CK2 subunit interaction. *Biochem J* 408:363-73.

Laudet, B., et al. (2008) Identification of chemical inhibitors of protein-kinase CK2 subunit interaction. *Mol Cell Biochem* 316:63-9.

Li, C., Liu, X., Lin, X. and Chen, X. (2009) Structure-activity relationship of 7 flavonoids on recombinant human protein kinase CK2 holoenzyme. *J Cent S Univ*.

Li, P.-F., et al. (2002) Phosphorylation by protein kinase CK2: a signaling switch for the caspase-inhibiting protein ARC. *Mol Cell* 10:247-58.

Lin, J., et al. (2002) A role for casein kinase 2alpha in the *Drosophila* circadian clock. *Nature* 420:816-20.

Lipinski, C.A., et al. (2001) Experimental and computational approaches to estimate solubility and permeability in drug discovery and development settings. *Adv Drug Del Rev* 46:3-26.

Litchfield, D.W. (2003) Protein kinase CK2: structure, regulation and role in cellular decisions of life and death. *Biochem J* 369:1-15.

Litchfield, D.W., Bosc, D., Canton, D.A., Saulnier, R.B., Vilk, G. and Zhang, C. (2001) Functional specialization of CK2 isoforms and characterization of isoform-specific binding partners. *Mol Cell Biochem* 227:21-9.

Llobet, D., et al. (2008) CK2 controls TRAIL and Fas sensitivity by regulating FLIP levels in endometrial carcinoma cells. *Oncogene* 27:2513-24.

Lorenz, P., et al. (1994) Requirement of casein kinase 2 for entry into and progression through early phases of the cell cycle. *Cell Mol Biol Res* 40:519-27.

Lou, D.Y., et al. (2008) The alpha catalytic subunit of protein kinase CK2 is required for mouse embryonic development. *Mol Cell Biol* 28:131-9.

Lozeman, F.J., et al. (1990) Isolation and characterization of human cDNA clones encoding the alpha and the alpha' subunits of casein kinase II. *Biochemistry* 29:8436-47.

Ma, H., et al. (2008) The challenge of selecting protein kinase assays for lead discovery optimization. *Expert Opin Drug Discov* 3:607-21.

Maier, B., et al. (2009) A large-scale functional RNAi screen reveals a role for CK2 in the mammalian circadian clock. *Genes Dev* 23:708-18.

Manning, G., et al. (2002) The protein kinase complement of the human genome. *Science* 298:1912-34.

Mantovani, A., et al. (2008) Cancer-related inflammation. *Nature* 454:436-44.

McDonnell, M.A., et al. (2008) Phosphorylation of murine caspase-9 by the protein kinase casein kinase 2 regulates its cleavage by caspase-8. *J Biol Chem* 283:20149-58.

Medina-Palazon, C., et al. (2007) Protein kinase CK2 phosphorylation of EB2 regulates its function in the production of Epstein-Barr virus infectious viral particles. *J Virol* 81:11850-60.

Meggio, F., Boldyreff, B., Marin, O., Pinna, L.A. and Issinger, O.-G. (1992) Role of the beta subunit of casein kinase-2 on the stability and specificity of the recombinant reconstituted holoenzyme. *Eur J Biochem* 204:293-7.

Meggio, F. and Pinna, L.A. (2003) One-thousand-and-one substrates of protein kinase CK2? *FASEB J* 17:349-68.

Meggio, F., et al. (1990) Ribofuranosyl-benzimidazole derivatives as inhibitors of casein kinase-2 and casein kinase-1. *Eur J Biochem* 187:89-94.

Montenarh, M. (1997) Das Wachstumssuppressorprotein p53, seine zellulären Partner und das Prostatakarzinom. *Aktuel Urol* 28:371-6.

Mottet, D., et al. (2005) Role for casein kinase 2 in the regulation of HIF-1 activity. *Int J Cancer* 117:764-74.

Münstermann, U., et al. (1990) Casein kinase II is elevated in solid human tumours and rapidly proliferating non-neoplastic tissue. *Eur J Biochem* 189:251-7.

Nie, Z., et al. (2008) Structure-based design and synthesis of novel macrocyclic pyrazolo[1,5-a] [1,3,5]triazine compounds as potent inhibitors of protein kinase CK2 and their anticancer activities. *Bioorg Med Chem Lett* 18:619-23.

Niefind, K., et al. (2001) Crystal structure of human protein kinase CK2: insights into basic properties of the CK2 holoenzyme. *EMBO J* 20:5320-31.

Niefind, K. and Issinger, O.-G. (2005) Primary and secondary interactions between CK2alpha and CK2beta lead to ring-like structures in the crystals of the CK2 holoenzyme. *Mol Cell Biochem* 274:3-14.

Niefind, K., et al. (1999) GTP plus water mimic ATP in the active site of protein kinase CK2. *Nat Struct Biol* 6:1100-3.

ole-MoiYoi, O.K. (1995) Casein kinase II in theileriosis. *Science* 267:834-6.

Olsen, B.B., et al. (2007) Emodin negatively affects the phosphoinositide 3-kinase/AKT signalling pathway: a study on its mechanism of action. *Int J Biochem Cell Biol* 39:227-37.

Olsen, B.B., et al. (2006) Purification and characterization of the CK2alpha'-based holoenzyme, an isozyme of CK2alpha: a comparative analysis. *Protein Expr Purif* 47:651-61.

Olsten, M.E.K. and Litchfield, D.W. (2004) Order or chaos? An evaluation of the regulation of protein kinase CK2. *Biochem Cell Biol* 82:681-93.

Olsten, M.E.K., et al. (2005) CK2 interacting proteins: emerging paradigms for CK2 regulation? *Mol Cell Biochem* 274:115-24.

Pagano, M.A., et al. (2008) The selectivity of inhibitors of protein kinase CK2: an update. *Biochem J* 415:353-65.

Pagano, M.A., et al. (2010) Cystic fibrosis transmembrane regulator fragments with the Phe508 deletion exert a dual allosteric control over the master kinase CK2. *Biochem J* 426:19-29.

Pagano, M.A., et al. (2004) 2-Dimethylamino-4,5,6,7-tetrabromo-1H-benzimidazole: a novel powerful and selective inhibitor of protein kinase CK2. *Biochem Biophys Res Commun* 321:1040-4.

Pagano, M.A., et al. (2007) Tetrabromocinnamic acid (TBCA) and related compounds represent a new class of specific protein kinase CK2 inhibitors. *ChemBioChem* 8:129-39.

Pallares, J., et al. (2009) CK2beta is expressed in endometrial carcinoma and has a role in apoptosis resistance and cell proliferation. *Am J Pathol* 174:287-96.

Perea, S.E., et al. (2008) CIGB-300, a novel proapoptotic peptide that impairs the CK2 phosphorylation and exhibits anticancer properties both in vitro and in vivo. *Mol Cell Biochem* 316:163-7.

Perea, S.E., et al. (2004) Antitumor effect of a novel proapoptotic peptide that impairs the phosphorylation by the protein kinase 2 (casein kinase 2). *Cancer Res* 64:7127-9.

Perera, Y., et al. (2009) Anticancer peptide CIGB-300 binds to nucleophosmin/B23, impairs its CK2-mediated phosphorylation, and leads to apoptosis through its nucleolar disassembly activity. *Mol Cancer Ther* 8:1189-96.

Pinna, L.A. (1990) Casein kinase 2: an 'eminence grise' in cellular regulation? *Biochim Biophys Acta* 1054:267-84.

Pinna, L.A. (1994) A historical view of protein kinase CK2. *Cell Mol Biol Res* 40:383-90.

Pinna, L.A. and Allende, J.E. (2009) Protein kinase CK2 in health and disease: Protein kinase CK2: an ugly duckling in the kinome pond. *Cell Mol Life Sci*.

(56) References Cited

OTHER PUBLICATIONS

Prowald, K., et al. (1984) Enhanced casein kinase II activity in human tumour cell cultures. *FEBS Lett* 176:479-83.
Prudent, R., et al. (2008) Identification of polyoxometalates as nanomolar noncompetitive inhibitors of protein kinase CK2. *Chem Biol* 15:683-92.
Prudent, R., Sautel, C.F. and Cochet, C. (2010) Structure-based discovery of small molecules targeting different surfaces of protein-kinase CK2. *Biochim Biophys Acta* 1804:493-8.
Ravi, R. and Bedi, A. (2004) NF-kappaB in cancer-a friend turned foe. *Drug Resist Updat* 7:53-67.
Roig, J., et al. (1999) Multiple forms of protein kinase CK2 present in leukemic cells: in vitro study of its origin by proteolysis. *Mol Cell Biochem* 191:229-34.
Ruzzene, M., et al. (2002) Protein kinase CK2 inhibitor 4,5,6,7-tetrabromobenzotriazole (TBB) induces apoptosis and caspase-dependent.
Ruzzene, M. and Pinna, L.A. (2010) Addiction to protein kinase CK2: A common denominator of diverse cancer cells? *Biochim Biophys Acta* 1804:499-504.
Ryu, M.Y., et al. (2008) Localization of CKII beta subunits in Lewy bodies of Parkinson's disease. *J Neurol Sci* 266:9-12.
Sale, E.M. and Sale, G.J. (2008) Protein kinase B: signalling roles and therapeutic targeting. *Cell Mol Life Sci* 65:113-27.
Salomoni, P. and Pandolfi, P.P. (2002) the role of PML in tumor suppression. *Cell* 108:165-70.
Salvi, M., et al. (2009) Extraordinary pleiotropy of protein kinase CK2 revealed by weblogo phosphoproteome analysis. *Biochim Biophys Acta* 1793:847-59.
Salvi, M., et al. (2006) Discrimination between the activity of protein kinase CK2 holoenzyme and its catalytic subunits. *FEBS Lett* 580:3948-52.
Sarno, S., et al. (2003) Biochemical and three-dimensional-structural study of the specific inhibition of protein kinase CK2 by [5-oxo-5,6-dihydroindolo-(1,2-a)quinazolin-7-yl]acetic acid (IQA). *Biochem J* 374:639-46.
Sarno, S., et al. (2001) Selectivity of 4,5,6,7-tetrabromobenzotriazole, an ATP site-directed inhibitor of protein kinase CK2 ('casein kinase-2'). *FEBS Lett* 496:44-8.
Sarno, S., et al. (2005) Development and exploitation of CK2 inhibitors. *Mol Cell Biochem* 274:69-76.
Sato, S., et al. (2000) Modulation of Akt kinase activity by binding to Hsp90. *Proc Natl Acad Sci U S A* 97:10832-7.
Scaglioni, P.P., et al. (2008) CK2 mediates phosphorylation and ubiquitin-mediated degradation of the PML tumor suppressor. *Mol Cell Biochem* 316:149-.
Schneider, C.C., et al. (2009) DMAT, an inhibitor of protein kinase CK2 induces reactive oxygen species and DNA double strand breaks. *Oncol Rep* 21:1593-7.
Schneider, C.C., et al. (2010) p53 is dispensable for the induction of apoptosis after inhibition of protein kinase CK2. *Prostate* 70:126-34.
Seldin, D.C., et al. (2005) CK2 as a positive regulator of Wnt signalling and tumourigenesis. *Mol Cell Biochem* 274:63-7.
Seldin, D.C. and Leder, P. (1995) Casein kinase II alpha transgene-induced murine lymphoma: relation to theileriosis in cattle. *Science* 267:894-7.
Seldin, D.C., et al. (2008) Gene targeting of CK2 catalytic subunits. *Mol Cell Biochem* 316:141-7.
Shi, X., al. et al (2001) A novel casein kinase 2 alpha-subunit regulates membrane protein traffic in the human hepatoma cell line HuH-7. *J Biol Chem* 276:2075-82.
Shimoyama, Y., et al. (2001) Characterization of secretory type IIA phospholipase A2 (sPLA2-IIA) as a glycyrrhizin (GL)-binding protein and the GL-induced inhibition of the CK-II-mediated stimulation of sPLA2-IIA activity in vitro. *Biol*.
Shin, S., et al. (2005) Caspase-2 primes cancer cells for TRAIL-mediated apoptosis by processing procaspase-8. *EMBO J* 24:3532-42.
Siemer, S., Stalter, G., Ziegler, M. and Issinger, O. (1996) Charakterisierung der Proteinkinase CK2 in menschlichen Nierentumoren. *Aktuel Urol* 27:1-5.
Singh, N.N. and Ramji, D.P. (2008) Protein kinase CK2, an important regulator of the inflammatory response? *J Mol Med* 86:887-97.
Slaton, J.W., et al. (2004) Induction of apoptosis by antisense CK2 in human prostate cancer xenograft model. *Mol Cancer Res* 2:712-21.
Stalter, G., et al. (1994) Asymmetric expression of protein kinase CK2 subunits in human kidney tumors. *Biochem Biophys Res Commun* 202:141-7.
Sugano, S. et al. (1999) The protein kinase CK2 is involved in regulation of circadian rhythms in *Arabidopsis*. *Proc Natl Acad Sci U S A* 96:12362-6.
Suzuki, Y., et al. (2008) Structure-activity relationships of pyrazine-based CK2 inhibitors: synthesis and evaluation of 2,6-disubstituted pyrazines and 4,6-disubstituted pyrimidines. *Arch Pharm (Weinheim)* 341:554-61.
Tawfic, S., et al. (2001) Protein kinase CK2 signal in neoplasia. *Histol Histopathol* 16:573-82.
Thornburg, W. and Lindell, T.J. (1977) Purification of rat liver nuclear protein kinase NII. *J Biol Chem* 252:6660-5.
Tiganis, T., et al. (1993) Casein kinase II beta-subunit inhibits the activity of the catalytic alpha-subunit in the absence of salt. *Biochim Biophys Acta* 1203:282-9.
Torres, J. and Pulido, R. (2001) The tumor suppressor PTEN is phosphorylated by the protein kinase CK2 at its C terminus. Implications for PTEN stability to proteasome-mediated degradation. *J Biol Chem* 276:993-8.
Trembley, J.H., et al. (2009) Protein kinase CK2 in health and disease: CK2: a key player in cancer biology. *Cell Mol Life Sci* 66:1858-67.
Tsuchiya, Y., et al. (2009) Involvement of the protein kinase CK2 in the regulation of mammalian circadian rhythms. *Sci Signal* 2:ra26.
Ubersax, J.A. and Ferrell, J.E. (2007) Mechanisms of specificity in protein phosphorylation. *Nat Rev Mol Cell Biol* 8:530-41.
Unger, G., et al. (2004) Protein kinase CK2 as regulator of cell survival: implications for cancer therapy. *Curr Cancer Drug Tar* 4:77-84.
Valero, E., et al. (1995) Quaternary structure of casein kinase 2. Characterization of multiple oligomeric states and relation with its catalytic activity. *J Biol Chem* 270:8345-52.
Vilk, G., et al. (2008) Protein kinase CK2 catalyzes tyrosine phosphorylation in mammalian cells. *Cell Signal* 20:1942-51.
Villar-Palasi, C. and Kumon, A. (1981) Purification and properties of dog cardiac troponin T kinase. *J Biol Chem* 256:7409-15.
Walsh, D.A., et al. (1968) An adenosine 3',5'-monophosphate-dependant protein kinase from rabbit skeletal muscle. *J Biol Chem* 243:3763-5.
Wang, G., et al. (2005) Downregulation of CK2 induces apoptosis in cancer cells—a potential approach to cancer therapy. *Mol Cell Biochem* 274:77-84.
Wang, L., et al. (2006) Electrochemical studies of the interaction of the anticancer herbal drug emodin with DNA. *J Pharm Biomed Anal* 42:625-9.
Wang, S. and Jones, K.A. (2006) CK2 controls the recruitment of Wnt regulators to target genes in vivo. *Curr Biol* 16:2239-44.
Willert, K., et al. (1997) Casein kinase 2 associates with and phosphorylates dishevelled. *EMBO J* 16:3089-96.
Xu, X., et al. (1999a) Murine protein kinase CK2: gene and oncogene. *Mol Cell Biochem* 191:65-74.
Xu, X., et al. (1999b) Globozoospermia in mice lacking the casein kinase II alpha' catalytic subunit. *Nat Genet* 23:118-21.
Yamada, M., et al. (2005) Inhibition of protein kinase CK2 prevents the progression of glomerulonephritis. *Proc Natl Acad Sci U S A* 102:7736-41.
Yan, J.X., et al. (1998) Protein phosphorylation: technologies for the identification of phosphoamino acids. *J Chromatogr A* 808:23-41.
Yang, Y., Cheng, P. and Liu, Y. (2002) Regulation of the *Neurospora* circadian clock by casein kinase II. *Genes Dev* 16:994-1006.
Yenice, S., et al. (1994) Nuclear casein kinase 2 (CK-2) activity in human normal, benign hyperplastic, and cancerous prostate. *Prostate* 24:11-6.

(56) References Cited

OTHER PUBLICATIONS

Yim, H., et al. (1999) Emodin, an anthraquinone derivative isolated from the rhizomes of *Rheum palmatum*, selectively inhibits the activity of casein kinase II as a competitive inhibitor. *Planta Med* 65:9-13.
Zandomeni, R., et al. (1986) Casein kinase type II is involved in the inhibition by 5,6-dichloro-1-beta-D-ribofuranosylbenzimidazole of specific RNA polymerase II transcription. J Biol Chem 261:3414-9.
Zien, P., et al. (2005) Tetrabromobenzotriazole (TBBt) and tetrabromobenzimidazole (TBBz) as selective inhibitors of protein kinase CK2: evaluation of their effects on cells and different molecular forms of human CK2. *Biochim Biophys Acta* 1754:271-80.
International Search Report and Written Opinion issued Sep. 30, 2011 for PCT Application PCT/EP2011/060433 filed Jun. 22, 2011 and published as WO 2011/161151 on Dec. 29, 2011 (Inventors—Jose et al // Applicant—Jose et al.) (7 pages).
International Preliminary Report on Patentability issued Dec. 28, 2012 for PCT Application No. PCT/EP2011/060433 filed Jun. 22, 2011 and published as WO 2011/161151 on Dec. 29, 2011 (Inventors—Jose et al // Applicant—Jose et al) (6 pages).

\* cited by examiner

Fig. 4
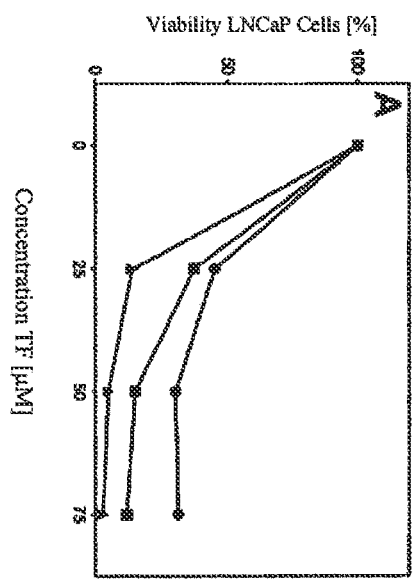
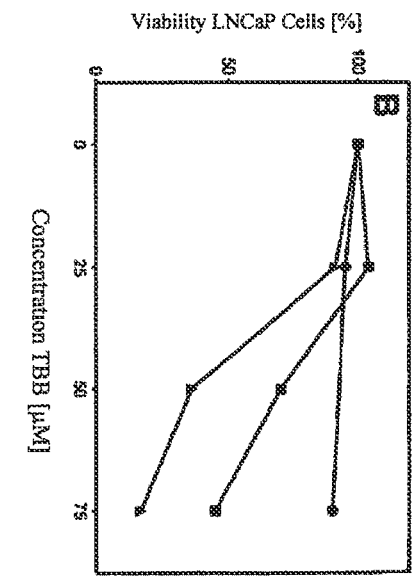

USE OF DIBENZOFURANONE DERIVATIVES TO INHIBIT KINASES

CROSS REFERENCE TO RELATED APPLICATIONS

The present application is a National Phase Application of International Application No. PCT/EP2011/060433, filed Jun. 22, 2011, which claims priority to German Patent Application No. 10 2010 025173.9, filed Jun. 25, 2010, which applications are incorporated herein fully by this reference.

The present invention relates to a pharmaceutical comprising a dibenzofuranone derivative as an active ingredient. Furthermore, the invention relates to the use of dibenzofuranone derivatives to inhibit kinases, in particular serine/threonine kinases, to the use of dibenzofuranone derivatives for producing pharmaceuticals and/or drugs for treatment, and to the use of dibenzofuranone derivatives as a diagnostic tool to investigate the role of protein kinases, in particular serine/threonine kinases, in particular the protein kinase CK2, in cellular processes, the pathogenesis of diseases, ontogenesis and/or other developmental biological phenomena or interrelationships.

The reversible phosphorylation of proteins is an important biological regulatory mechanism which influences nearly every aspect of life on a cellular level. In 1992, Edmond H. Fischer and Edwin G. Krebs were awarded the Nobel Prize for Medicine for their pioneering work which made a major contribution to recognition of this fact (Fischer, 1993; Krebs, 1993). The motivation for research into protein phosphorylation developed at the beginning of the 1950s from the observation that rapidly proliferating tissue, in particular certain tumour cells, possessed a large quantity of "phosphoproteins" which, moreover, were rapidly transformed (Kennedy and Smith, 1954). Since phosphatases were already known to be dephosphorylating enzymes, mediators for protein phosphorylation were sought. The first phosphoproteins to be investigated in this respect were dietary proteins such as phosvitin from egg yolk and casein from milk because they were easy to isolate by precipitation reactions. Burnett and Kennedy identified the first "protein phosphokinases" in 1954 using casein (Burnett and Kennedy, 1954). These "casein kinases" were most probably what are now known as the protein kinases CK1 and CK2 (Pinna, 1994). However, the physiological function of these two enzymes was still unknown; for this reason, scant attention was initially paid to this discovery. Just a year later, this changed with the discovery of glycogen-phosphorylase-b-kinase (now known as "phosphorylase-kinase") by Fischer and Krebs (Krebs and Fischer, 1956). Identification of this key regulatory enzyme for glycogen metabolism boosted protein kinase research, but its focus shifted from cancer research and onto research into protein kinases in the context of metabolic processes. Since that time, research into protein kinases has constantly been growing in importance. The discovery and investigation of cAMP-dependent protein kinase, PKA (Walsh et al., 1968), cyclin-dependent protein kinases, mitogen-activated protein kinases and the discovery of several receptor tyrosine kinases (Fischer, 1993; Krebs, 1993) showed that phosphorylation constitutes a general regulatory principle. With a plethora of consequences. Thus, phosphorylation can, for example, increase or reduce the biological activity of proteins, mark them for degradation and influence their stability. Furthermore, phosphorylations and dephosphorylations enable or block transport between cell compartments or interaction between proteins (Cohen, 2002a). The essential reaction which is catalysed by protein kinases is the transfer of phosphate residues from a donor, usually the γ-phosphate of adenosine triphosphate (ATP), to the nucleophilic centre of specific protein-bound amino acid side chains. In eukaryotes, phosphorylations of serine, threonine and tyrosine residues primarily occurs (O-phosphates) (Ubersax and Ferrell, 2007). Furthermore, phosphates of lysine, arginine (Yan et al., 1998) and histidine residues (Klumpp and Krieglstein, 2005) (N-phosphates) have been found; relatively little is as yet known about their function.

In the human genome, 518 homologous genes have been identified which potentially code for protein kinases. The term human "kinome" is now used to describe this. A generally accepted classification of the human kinome is shown in FIG. 1. Currently, it is assumed that approximately a third of all proteins of the 20000 to 25000 human genes are phosphorylated. The totality of these phosphorylated proteins is termed the phosphoproteome (Manning et al., 2002). Since parts of each protein can be multi-phosphorylated by different kinases, each protein kinase has on average approximately 20 substrates (Cohen, 2002a). Although the primary structures of protein kinases can differ substantially in parts, the catalytic core of protein kinases is highly conserved and forms a bilobal tertiary structure (Cheek et al., 2002; Cheek et al., 2005). This consists of an N-terminal segment with a plurality of folded β-sheets, a "hinge region" containing the active centre, and an α-helix-rich C-terminal domain.

Although they were among the first protein kinases to be discovered, CK2 initially did not attract much attention. Fischer and Krebs' Nobel lecture made mention of them only in a sub-paragraph (Fischer, 1993; Krebs, 1993). As a result, research into the as yet not completely explained physiological functions of the protein kinase CK2 was on a rather small scale. This may also be a reason why they have been called by different names in the more than 55 years since their discovery.

In addition to the original term "protein phosphokinase" used by Burnett and Kennedy, in the literature, the enzyme has been denoted as, for example, nuclear protein kinase NII (Thornburg and Lindell, 1977), eIF-2β-kinase (DePaoli-Roach et al., 1981), troponin-T-kinase (Villar-Palasi and Kumon, 1981), casein kinase TS (Deana et al., 1978) or even casein kinase II (Prowald et al., 1984). In 1994, at a conference of leading CK2 researchers, it was finally decided to use the term "protein kinase CK2" or the acronym "CK2" as the descriptor for this protein kinase (Ahmed et al., 1994).

Human serine/threonine protein kinase CK2 forms a heterotetrameric quarternary structure which is now described in the literature as a holoenzyme. It is present as a complex of catalytic (CK2α) and non-catalytic (CK2β) subunits in a $β_2β_2$-stoichiometry. In addition to the most frequently occurring 44 kDa catalytic α-subunit, there are two other isoforms of this subunit (α', 38 kDa (Lozeman et al., 1990) and α", 44 kDa (Shi et al., 2001)). These isoforms also exhibit catalytic activity, but have not been investigated as intensively (Litchfield et al., 2001). The 26 kDa β-subunit has a zinc finger domain, which enables dimerization of two β-monomers. The dimer forms an anchor point for oligomerization of the enzyme (Graham and Litchfield, 2000). Two α-monomers bind to the β-dimeric core structure such that in the complex, they do not come into direct contact with each other (Niefind et al., 2001). This oligomerization occurs spontaneously and is highly stable. There are also indications, however, that in vivo, CK2 does not exist exclusively as a tetrameric holoenzyme. Its isolated subunits may also have a physiological function (Faust and Montenarh, 2000; Bibby and Litchfield, 2005). Furthermore, annular or filamentary aggregates of several CK2 holoenzymes have been observed in vitro (Valero et al., 1995; Niefind and Issinger, 2005).

The classification of CK2 is based on the catalytically active α-subunit. Because of their sequence homology, they are assigned to the CMGC protein kinase family (see FIG. 1). This comprises cyclin-dependent kinases (CDK), mitogen-activated protein kinases (MAP kinases), glycogen synthase-kinase 3-like kinases (GSK3) and CDK-like kinases (CLK). The closest relatives to CK2 in this family are MAP kinases, CDKs and GSK3 (Manning et al., 2002). Sequence identity of CK2α with these enzymes is up to 35%.

In contrast to other protein kinase representatives, CK2 has several peculiarities. In recent years, the number of experimentally confirmed substrates has risen almost exponentially and at the moment stands at well over 300 (Meggio and Pinna, 2003; Salvi et al., 2009). This property, denoted "pleiotropy" is highly unusual for protein kinases and is reflected in the multiple descriptors used for this enzyme, which fact was mentioned above.

Most protein kinases exhibit no or only low basal activity. Activation thereof is mostly strictly regulated and occurs by means of a stimulus, an effector or a physiological status (Blume-Jensen and Hunter, 2001). In contrast, CK2 has high cellular activity (Pinna, 1990). Both isolated CK2α and the tetrameric holoenzyme are constitutively active. Until now, at the protein level, no typical mechanism is known for regulating CK2 activity. Instead, in recent years, a multi-layer model for the regulation of CK2 has become established which incorporates the majority of empirical knowledge about the complex regulation of CK2 and offers initial attempts at elucidations (Filhol and Cochet, 2009). It is assumed that the level of CK2 activity is controlled by spatiotemporal regulation. As an example, the substrate specificity of CK2α can change after tetramerization to the holoenzyme or into higher forms of association (Meggio et al., 1992; Valero et al., 1995; Salvi et al., 2006). This effect was also observed after intermolecular associations with various substrates or binding partners (Olsten and Litchfield, 2004; Olsten et al., 2005). In this manner, the activity with respect to a specific substrate can be modulated by allosteric effectors. In addition, dynamic localization of CK2 or its subunits occurs between different subcellular compartments, primarily between the nucleus and cytoplasm (Faust and Montenarh, 2000). Thus, the activity of CK2 can be varied in specific compartments, while the total activity of the cell remains constant. A further atypical feature of CK2 is its dual co-substrate specificity for ATP and GTP (Niefind et al., 1999). Both molecules can be used almost equally as phosphate donors. With the exception of Src kinase (Graziani et al., 1983) and EGF-receptor kinase (Carpenter et al., 1979), this is not possible with any other protein kinase. New studies also show that under certain circumstances, CK2 can phosphorylate tyrosine residues as well as serine and threonine residues. In addition to the dual co-substrates, it can also have dual substrate specificity (Vilk et al, 2008).

In general, CK2α is acidophilic, i.e. the sequence environment of the substrate in which the residue (n) to be phosphorylated is found must comprise acidic amino acids. A minimum consensus sequence for substrates is (n)-X-X-(D/E/Sp/Tp) (Meggio and Pinna, 2003). In position (n+3), a negatively charged amino acid side chain appears to be essential for substrate recognition. This can also be represented by a phosphorylated serine (Sp) or threonine (Tp). Further negative charges, above all in position (n+1), are necessary. A model substrate for the investigation of CK2 activity which has been established in several research groups is the peptide with sequence RRRDDDSDDD (Kuenzel et al, 1987; Olsen et al., 2006; Schneider et al., 2010); it is also used in this work.

In stark contrast to the α subunit, there is no homologue in the human proteome for the β subunit of CK2. There is a very high degree of conservation between the various species (Allende and Allende, 1995), which implies an important functional role for this protein. The literature currently describes it as a "regulatory subunit" since it influences the substrate specificity and thus the activity of the CK2 holoenzyme can be modulated (Meggio et al, 1992; Tiganis et al, 1993; Salvi et al., 2006). On the other hand, it is clear from the crystalline structure of the holoenzyme that CK2β presumably has no direct influence on the catalytic key structures of CK2α (Niefind et al., 2001). A role as "contact mediator" for substrates can be envisaged for CK2β. It has long been accepted that a drastically increased stability and reduced protease sensitivity occurs with CK2β induced oligomerization (Meggio et al, 1992).

Several factors support an important physiological role for CK2. Its amino acid sequence is highly conserved across species boundaries. Furthermore, CK2 activity can be demonstrated in almost all tissues, cell types and in many cell compartments. Even the large number of interaction partners, as well as its constitutive activity, suggests an important role for it. We shall now set out concrete factors about the key functions of CK2 in a cellular context. The effects of CK2 in various signal transduction pathways and their consequences will be discussed below.

CK2 differs functionally from most other protein kinases which carry out this function at a specific location within a strictly hierarchical "vertical" signal transduction pathway in binary mode. Meggio and Pinna formulated the postulation that information transfer via CK2 instead occurs horizontally and ties together several signal pathways (Meggio and Pinna, 2003). Thus, CK2 could be of fundamental significance to basal cell functions. Its ubiquitous presence, its highly constitutive activity and its more than 300 substrates suggest that CK2 is actually participating in keeping the phosphoproteome at a level that is important for life (Barz et al., 2003). Metaphorically speaking, CK2 is acting as a team-orientated key player rather than as a highly specialized goal scorer.

In contrast to this rather global, highly nonspecific function, current results are indicating to a greater and greater extent that CK2 has a role to play in biorhythms. Thus, a high expression of CK2α was detected in the cytoplasm of neurons of *Drosophila melanogaster* which has a pacemaker function for the internal clock. Heterozygous CK2α-deficient fruit flies have a so-called timekeeper phenotype: they have an approximately 1 h longer rhythm (Lin et al., 2002). Results of similar in vivo studies in plants (*Arabidopsis*) (Sugano et al., 1999), fungi (*Neurospora*) (Yang et al., 2002), mice (Tsuchiya et al., 2009) and in human cells (Maier et al., 2009) also show a direct relationship between CK2 activity and biorhythms. CK2 appears to be an important conserved element which links control of the biorhythms in these three phylogenetic kingdoms.

The significance of CK2 to life in various organisms has been proved by knocking out expression of the CK2 gene. In mice, knockout of CK2β (Buchou et al., 2003), and of CK2α (Lou et al., 2008) resulted in embryonic lethality. In the latter case, the mice died in embryogenesis with developmental heart and neural tube defects (Seldin et al., 2008). Deletion of CK2α' in male mice could be compensated for during the embryonic development of CK2α, but later resulted in defective spermatogenesis and infertility (Xu et al., 1999b; Escalier et al., 2003). Deletion experiments with *Saccharomyces cerevisiae* (Glover, 1998) and human fibroblasts (Lorenz et al., 1994) confirmed the importance of CK2 to life. Absence of CK2 activity in these experiments resulted in cell cycle arrest.

Recently, it has been shown that phosphorylation of eIF5 ("eukaryotic translation initiation factor 5") by CK2 constitutes an essential event in order for the cell cycle to progress (Homma and Homma, 2008). In that investigation, the functional activation of CK2 could be correlated with translocation from the cytoplasm into the cell nucleus. These results imply that CK2 plays a decisive role in regulation of the cell cycle and cell proliferation.

Other indications point to a key function of CK2 being a negative regulator of apoptosis. In apoptosis, specific proteolytic events play a central role driven by caspases. It has been shown for some caspase substrates that their sensitivity for caspase-mediated degradation following phosphorylation by CK2 is greatly reduced (Desagher et al., 2001; Ruzzene et al., 2002). A similar consensus sequence of caspase and CK2 substrates could be responsible (Litchfield, 2003). In addition, CK2 can also directly inhibit the activity of caspases. A phosphorylation of murine caspase-9 by CK2, for example, protects against its degradation by caspase-8 (McDonnell et al., 2008). Further, CK2-mediated phosphorylation of caspase-2 inhibits its dimerization and thus inhibits its activation (Shin et al., 2005). The phosphorylation of ARC ("apoptose repressor with caspase recruitment domain") by CK2 is a prerequisite for its effective inhibition of caspase-8 (Li et al., 2002). The postulated correlation of CK2 activity and the suppression of apoptosis were proved by cell culture experiments in which the activity of CK2 was brought to a slightly lower level (Unger et al., 2004; Wang et al., 2005). These cells were substantially more sensitive to apoptosis-inducing stimuli than cells with a normal degree of CK2 activity. In contrast, over-expression of CK2 made cells more resistant against these stimuli (Ahmad et al., 2008).

CK2 was directly or indirectly linked to a series of diseases; some are listed in Table 1. This shows essential information for various types of dysregulation. In the case of viral diseases, CK2 activity of viral proteins is sometimes used parasitically (Filhol and Cochet, 2009). The enormous number of implications of this enzyme which have been found is presumably based on the mentioned multitude of substrates and the pleiotropic effects resulting therefrom. Knowledge of the role of CK2 in this and other diseases is discussed in a review article by Guerra and Issinger (2008). The most and best-researched indications of a pathological effect of dysregulated CK2, however, are to be found in the context of cancers. This relationship will be illustrated below from a number of perspectives which are drawn from rational and also from empirical facts.

TABLE 1

Overview of human non-oncological diseases which indicate the involvement of CK2

| Type of disease | Examples/pathogen | Reference |
|---|---|---|
| Neuro-degeneration | Alzheimer | (Blanquet, 2000) |
| | Parkinson | (Ryu et al., 2008) |
| | Spongiform encephalopathy | (Chen et al., 2008) |
| Inflammation processes | Autoimmune diseases (eg RA) | (Shimoyama et al., 2001) |
| | Glomerulonephritis | (Yamada et al., 2005) |
| | Cystic fibrosis | (Pagano et al., 2010) |
| Protozoan infections | Chagas (*Trypanosoma cruzi*) | (Augustine et al., 2006) |
| | Malaria (*Plasmodium falciparum*) | (Hora et al., 2009) |
| | Toxoplasmosis (*Toxoplasma gondii*) | (Delorme et al., 2003) |
| Viral infection | EBV | (Medina-Palazon et al., 2007) |
| | HIV | (Caples et al., 2006) |
| | HPV | (Chien et al., 2000) |
| Vascular diseases | Atherosclerosis | (Harvey et al., 2007) |

Many years of cancer research on medical-anatomic, cellular, biochemical and molecular genetic fronts have given rise to an immeasurable number of facts and postulations about the onset of disease which now cannot be fully appreciated due to their complexity. As a result, oncogenesis has to be described in a few core principles which are at the basis of most cancers. In general, it is assumed that carcinogenesis is a multi-step process which leads to some cancer-acquired capabilities which together cause an oncogenic transformation. In addition to the modified reaction to external stimuli of the microenvironment, a loss of autonomous cell control mechanisms has to occur. At the beginning of the millennium, Hanahan and Weinberg formulated six hallmarks for the manifestation of a tumour: 1) self-sufficiency in growth signals; 2) insensitivity to growth signals; 3) suppression of apoptosis; 4) limitless reproduction potential; 5) sustained angiogenesis; and 6) invasive growth and metastasis (Hanahan and Weinberg, 2000). Many of these capabilities are favoured by an elevated CK2 level. As already mentioned, an increased CK2 activity perturbs control of the cell cycle and cell growth and has anti-apoptotic effects. In the parasitic cattle disease theileriosis (East African fever), a substantially elevated CK2 activity, which was in agreement with these observations, was observed, which was accompanied by a great proliferation of lymphocytes (ole-MoiYoi, 1995). Further, a link between CK2 activity and angiogenesis has been found (Mottet et al., 2005; Kramerov et al., 2008).

In addition to these direct tie-ups between the hallmarks of cancer and CK2 activity, there are further tie-ups which have causal relationships which are occasionally indirect and less clear. As an example, perturbed biorhythms, the regulation of which can be influenced by CK2, has been linked to cancers (Eu and Lee, 2003). Further, CK2 has recently been postulated as an important regulator in inflammation reactions (Singh and Ramji, 2008), which could be linked to its role in the NF-κB pathway (FIG. 1C), described below. The significance of inflammation processes in oncogenesis has already been discussed in detail (Mantovani et al., 2008). These examples show that many of the cellular features influenced by CK2 activity agree with the hallmarks of oncogenesis.

Several investigations have suggested a direct link between CK2 and cellular processes relevant to cancer. Thus, CK2 interacts by various mechanisms with several proteins and signal transduction pathways which have direct effects on oncogenesis. This explains some of the features of cancer influenced by CK2 on a molecular level.

The Wnt signal pathway (FIG. 1A) drives embryogenesis, cell differentiation and cell division by the activation of transcription factors. Target genes in this signal pathway belong to the most highly mutated genes in human tumours. The conventional Wnt signal pathway is activated by an extracellular Wnt factor which binds to a transmembrane receptor from the Fizzeld family (Fz). Subsequently, Fz dimerizes with the coreceptor LRP and activates cytoplasmic dishevelled (Dsh) proteins. Phosphorylation of Dsh is mediated by CK2 and is important for its inhibiting effect on glycogen synthase-kinase (GSK3β). By inhibiting GSK3β, β-catenin can conduct the Wnt signal into the cell nucleus instead of being degraded after GSK3β phosphorylation (Willert et al., 1997). It is now thought that β-catenin and its receptor, the TCF/LEF transcription factor, are themselves CK2 substrates and CK2-mediated phosphorylation promotes their activity (Wang and Jones, 2006). Reinforcement of the Wnt signal increases the strength of expression of the Wnt target gene. These target genes also include several proto-oncogenes. An increased CK2 activity can lead to reinforcement of the Wnt signal pathway via the lateral mechanisms shown and to increased expression of proto-oncogenes to promote oncogenesis (Seldin et al., 2005; Dominguez et al., 2009).

Further CK2 substrates can be found in the PI3K/Akt pathway (FIG. 1B). In general, activation of this signal pathway has an anti-apoptotic effect (Sale and Sale, 2008; Chalhoub and Baker, 2009). PTEN ("phosphatase and tensin homologue deleted on chromosome 10") is a tumour suppressor and one of the CK2 substrates which are ensconced at a higher level in this hierarchichal pathway. In the activated form, PTEN constitutes a negative regulator of this pathway. Phosphorylation by CK2 has negative effects both on its stability and also on its phosphatase activity (Torres and Pulido, 2001). A second central component of this signal pathway is Akt, which is also known as protein kinase B. A CK2-mediated phosphorylation potentializes the activity of Akt (Di Maira et al., 2005). It is assumed to underpin complex formation of Akt with the chaperone Hsp90, which results in stabilization of the active status of Akt (Sato et al., 2000). Both effects of CK2, weakening of PTEN and activation of Akt, lead to a reinforcement of the PI3K/Akt pathway. Together with the described inhibition of caspases, then, CK2 has an overall role as an anti-apoptotic regulator; its dysregulated activity develops oncogenetic potency.

A further signal transmission pathway which can be modulated by CK2 activity is the NF-κB pathway (FIG. 1C). In addition to its main task in inflammation processes, this pathway was also linked to pro-proliferative and anti-apoptotic activity as well as to cell transformation. In this manner, it influences some of the cited hallmarks of oncogenesis (Ravi and Bedi, 2004). In this case too, CK2 reinforces the signal pathway, via various mechanisms by lateral interaction with IKK, IκB and NF-κB (Dominguez et al., 2009).

In the context of this cascade signal transmission, it has also been shown that CK2 has no clear role in a specific physiological function. The signal pathways described primarily influence cell differentiation, proliferation and survival, i.e. precisely those cellular capabilities which are observed to be manifested defectively in oncogenesis. The influence of CK2 in this case is lateral, and thus leads to a modulation in the "vertical" flow of information and in all cases potentializes the original stimulus (FIG. 1).

CK2 thus constitutes a kind of primary regulator and at the same time is a binder of essential cell functions. Thus, it is hardly surprising that a change in its overall cellular activity has profound effects. In fact, in investigations into many cancer types, a correlation between increased CK2 activity and induction or strengthening of the described signal pathways has been established (Seldin et al., 2005; Guerra, 2006; Di Maira et al., 2009; Dominguez et al., 2009).

Most CK2 substrates are not integrated into such signal pathways. Some are directly involved in carcinogenesis. Transcription factor p53 is known as the "guardian of the genome" (Lane, 1992). After induction by cell stress, it determines the biosynthesis of proteins which stop the cell cycle, inhibit angiogenesis, induce apoptosis or belong to the cellular DNA repair system. The p53-mediated effects in total work against oncogenesis and p53 is considered to be one of the most important tumour suppressor proteins (Brown et al., 2009). In actual fact, the inhibition of p53 appears to be a key factor in cancer, since in over 50% of human tumours, there is a change in the p53 gene which weakens its effect or completely suppresses it (Montenarh, 1997). In addition to a direct phosphorylation of p53 by CK2, non-enzymatic interactions of CK2α and CK2β have been found with p53, which influence the function of p53 and CK2. In addition, CK2 also interacts with p53-regulated enzymes such as Mdm2 (Allende-Vega et al., 2005). All of these CK2-mediated effects inhibit the activity of p53. A further CK2 substrate which is relevant to cancer is the tumour suppressor PML ("promyelocytic leukemia tumor suppressor")(Salomoni and Pandolfi, 2002). A ubiquitin-mediated degradation of PML in cancer cells is a direct consequence of phosphorylation by increased CK2 activity (Scaglioni et al., 2008).

Even though the mechanisms of the interactions between CK2 and its substrates are so different, the result in the described cases is always the same: in healthy cells, the activity of CK2 is important for normal cell function. However, increasing it leads to a weakening of cellular defence mechanisms against carcinogenesis and favours conditions which promote oncogenesis.

Investigations into CK2 levels in cancer cells provide the clearest indications so far of a role of CK2 played in cancer. In all cancer tissues that have so far been investigated as regards CK2, an increased expression of CK2 or an increased CK2 activity compared with the corresponding healthy tissue was found (Trembley et al., 2009). As an example, in human breast carcinomas, a CK2 activity was observed which, on average, was a factor of 10 higher than in healthy breast tissue (Landesman-Bollag et al., 2001a; Landesman-Bollag et al., 2001b). The CK2α concentration in these tumours was also significantly higher. In another study, the activity and expression of CK2 in histologically different kidney tumours was compared with ipsilateral normal tissue (Siemer et al., 1996). Upon quantitative investigation of the subunits, in all kidney tumours, an increase in both the α and in the β subunit was detected. The activity of CK2 in the various kidney tumours was, on average, increased by a factor of 2. The largest increase in activity of 375% occurred with the malignant nephroblastoma. In a benign oncocytoma on the other hand, the increase was just 59%, however. In addition, in these tumours there were indications of a heterogeneous expression of both CK2 subunits compared with normal tissue (Stalter et al., 1994), which could also be observed in other investigations (Faust et al., 1999). An increased level of CK2 has also been observed in many other cancers (Guerra and Issinger, 2008), including carcinoma of the colon (Münstermann et al., 1990), leukaemia (Roig et al., 1999), in tumours of the lungs (Daya-Makin et al., 1994), the endometrium (Llobet et al., 2008; Pallares et al., 2009), and the prostate (Yenice et al., 1994; Laramas et al., 2007). Moreover, various studies indicate a direct relationship between the degree of CK2 activity increase and the malignancy of the cancer (Tawfic et al., 2001; Unger et al., 2004). Because of this, CK2α has been discussed as a prognostic marker for various types of cancer (Kim et al., 2007; Laramas et al., 2007).

It is still unclear as to how and in what way neoplastic transformation instigates the increase in CK2 activity. It does not appear to be a consequence of the great proliferation of cancer cells which even in pre-cancerous dysplasia can be shown to have an increased CK2 activity (Faust et al., 1999).

In contrast to oncogenes which are relevant to cancer or tumour suppressor genes, interestingly, until now no mutations of the CK2 gene have been found which lead to hyperactivity of the enzyme. The main mechanism for the increase in activity of CK2 in tumour cells thus seems to be the increase in the quantity of enzyme because of increased expression of the CK2 gene. In addition, the currently incompletely understood regulation of CK2 may play a role (Guerra and Issinger, 1999, 2008).

In addition to these descriptive studies, in complementary investigations, the expression of CK2 in model systems was artificially increased in order to observe the pathophysiological consequences. Transgenic mice with an increased level of lymphocytary CK2 expression showed a significantly increased incidence of leukaemia. From the age of 6 months they developed lymphoma with an incidence of 6-15% per year (Seldin and Leder, 1995; Kelliher et al., 1996). When in addition to CK2α, an oncogen, for example c-myc or TAL-1, is over-expressed, this considerably strengthened the pathogenic phenotype compared with the appropriate singular over-expression. Such a synergistic oncogenic effect can be also shown by inhibition of the tumour suppressor p53 in combination with increased levels of CK2. Mice which are heterozygous for p53 and have increased CK2α expression develop T cell lymphoma on average twice as quickly as p53-heterozygous mice (Landesman-Bollag et al., 1998). Other transgenic mice with an increased CK2α expression in the mammary glands quickly developed hyperplasia and neoplasias in this tissue. In transgenic mouse models with only increased CK2α expression, tumour development was latent (Landesman-Bollag et al., 2001a). This indicates that elevated CK2 activity alone is not sufficient for oncogenesis. The possibility that the transformation of these mouse lymphocytes is triggered by a multi-step process has also been discussed (Xu et al., 1999a; Landesman-Bollag et al., 2001b). The observed faster oncogenesis after further increased oncogene or reduced tumour suppressor expression supports this hypothesis. In combination with the observations described above, it can be assumed that a surplus CK2 activity creates a cellular medium which boosts uncontrolled growth and opposes apoptosis. Such cells are robbed of most of the natural defence mechanisms against secondary cancer-forming events and thus suffer neoplastic transformation faster. It is stressed that CK2 itself does not constitute an oncoprotein (Trembley et al., 2009). If the dependency of increased activity of CK2 does not occur at the beginning of oncogenesis, it appears that many tumour cells develop this with further progress (Ruzzene and Pinna, 2010).

In various studies, the inhibition of CK2 can limit the growth of tumour cells or even cause remission of the tumour phenotype. Effects of suppressing CK2 biosynthesis and the resulting low CK2 concentration in the tumour tissue has, for example, been investigated in the murine xenograft model of the prostate carcinoma (Slaton et al., 2004). CK2 expression in vivo was reduced by intra-tumour injection of antisense RNA against CK2α. A single administration of 5 μg of antisense RNA reduced tumour growth within 7 days to 30-40%. Increasing the dose to 20 μg resulted after 7 days in complete regression of the tumour. These impressive results confirm the dependency of the tumour on CK2α. However, they do not explain whether catalytic activity or non-catalytic interactions are responsible for the tumour-boosting effect. Although antisense oligonucleotides are valuable in basic research, opportunities for using them therapeutically in cancer are limited. For clinical use, small molecular inhibitors are still being developed. In some experiments, the effect of cell-permeable small molecular CK2 inhibitors have been investigated on cultivated cancer cell lines. Thus, DRB (Farah et al., 2003), emodin (Olsen et al., 2007), TBB (Sarno et al., 2001), TBI (Zien et al., 2005), DMAT (Pagano et al., 2004), IQA (Sarno et al., 2003) and TBCA (Pagano et al., 2007) induced apoptosis and were cytotoxic. The effects of these ATP-competitive inhibitors most probably result from inhibition of the increased CK2 activity in the cancer cells. For some inhibitors such as emodin, TBCA and TBB, moreover, inhibition of angiogenesis was observed (Kramerov et al., 2008). A reduction in CK2 activity thus opposes some hallmarks of oncogenesis.

All current knowledge bears witness to the dependency of cancers on increased CK2 activity. Overall, the results set out here substantiate the assumption that catalytic activity is primarily responsible for the pathological effects of increased CK2 levels in cancers. Furthermore, it has been able to be shown that an inhibition of CK2 activity works against the tumour phenotype. Thus, it follows that CK2 is an attractive target molecule for the development of therapeutic intervention means in cancers.

A high protein kinase activity can be opposed on a protein level by small molecular substances. The first inhibitors of protein kinases were identified more than 25 years ago and initially primarily used to explain the physiological function of this class of enzymes (Hidaka et al., 1984). The overwhelming success of imatinib inspired the hope for a broad clinical use of this group of substances against oncological diseases (Druker, 2009). The development of the protein kinase inhibitor imatinib was aimed at inhibiting the oncoprotein Bcr-Abl. Since this ground-breaking work, the research and development of protein kinase inhibitors has grown greatly in significance. According to current estimates, more than 30% of industrial substance development programmes concern protein kinase inhibitors (Cohen, 2002b; Eglen and Reisine, 2009). This class of substances has thus become one of the most important focusses of pharmaceutical research.

In order to determine the potential of an inhibitor, a reliable and meaningful activity test for the target enzyme is vital. The currently most widely used method to assay the activity of protein kinases is a radiometric test (Hastie et al., 2006). In published investigations into CK2 activity, a radiometric filter binding test is almost exclusively used as a standard method (Bretner et al., 2008; Schneider et al., 2009). This is based on quantifying the transfer of [$^{32}$P]-labelled γ phosphate of ATP to a seryl side chain of a peptide or protein substrate by CK2. A peptide that is used for many CK2 activity tests has the amino acid sequence RRRDDDSDDD and can bind to a cation exchange filter paper via the N-terminal arginine. Unreacted γ-[$^{32}$P]-ATP does not bind and can be washed out. The remaining radioactivity can be quantified and is proportional to the CK2 activity (Hastie et al., 2006). The radiometric detection of phosphotransfer is a basic principle which allows the activity of nearly all protein kinases to be determined. For this reason a CK2 substrate has to be used which can be immobilized for analysis, for example by ion interactions. Further, new γ-[32P]-ATP is needed at regular short intervals since the half-life of the $^{32}$P isotope is short. Thus, all of the radioactivity decays away. A radiometric kinase test can thus only be automated at great expense and is extremely expensive, particularly with small sample throughputs.

A number of alternative methods exist for determining the activity of protein kinases non-radiometrically (Jia et al., 2008; Ma et al., 2008). To measure the CK2 activity effectively, however, only a single non-radiometric test procedure has been described in the literature (Hung et al., 2009). This commercially available reagent kit ("CK2 Kinase Assay/Inhibitor Screening Kit", CycLex, Nagano, Japan) uses a peroxidase-coupled anti-phospho-p53-antibody which binds to Ser-46 in p53, as long as this side chain has been phosphorylated by CK2. This antibody acts as a reporter in a homogeneous ELISA. After incubation with the chromogenic substrate tetramethylbenzidine, it develops a coloured product which can be detected spectroscopically. By measuring the absorption, the quantity of transformed CK2 substrate can be quantified. Comparative investigations of CK2 activity with this test procedure have not been carried out, however. Until now, only a few semi-quantitative assays have been described (Hung et al., 2009). In the meantime, indirect tests exist, for example luminometric detection of the decay of the co-substrate AT? during the kinase reaction using luciferase ("Kinase-Glo assay", Promega, Mannheim).

For the inhibition studies undertaken in this work, a test was required which satisfied several requirements. It had to dispense with radioisotopes and be as simple as possible to carry out and therefore be reproducible and robust. Furthermore, it should be suitable for series of investigations of low molecular weight compounds and in the ideal case allow $IC_{50}$ values to be determined. The results should not only be comparable between themselves, but also permit a comparison with data in the literature. None of the published CK2 inhibition tests satisfied these requirements.

The currently most potent ($IC_{50}<1$ μM) and best-investigated inhibitors for CK2 are low molecular weight substrates which address the co-substrate binding site of the active centre (FIG. 3). Current reviews of currently known inhibitors for CK2 are to be found in publications by Bortolato et al. (2008), Battistutta (2009), Cozza et al. (2010) and Prudent and Cochet (2010). A few important compounds with different basic frameworks will be presented below by way of example.

Many currently known CK2 inhibitors are derived from the benzimidazole framework of DRB (5,6-dichloro-1-β-D-ribofuranosylbenzimidazole). DRB is an adenosine analogue and has been identified as one of the first CK2 inhibitors (Zandomeni et al., 1986). Its high $IC_{50}$ of 13 μM and medium selectivity among various protein kinases, however, led to its current low relevance as a CK2 inhibitor. Structural variations of DRB, on the other hand, led to more potent compounds. This shows that the sugar residue does not play a role in inhibition; however, exchanging two chlorine for four bromine substituents on the benzimidazole framework considerably increases the inhibitory potential (Meggio et al., 1990). This led to the development of the two halogenated benzimidazole derivatives TBI (4,5,6,7-tetrabrombenzimidazole) and TBB (4,5,6,7-tetrabrombenzotriazole, FIG. 2), which both have an $IC_{50}$ of about 1 μM. More important than the potency, however, was good cell permeability and a relatively high selectivity which, inter alia, was shown by TBB in investigations with 33 other protein kinases (Sarno et al., 2001). These properties made TBB the inhibitor of choice in research into the biological functions of CK2. Further variations in the TBI framework have recently been identified by the inhibitor DMAT (2-dimethylamino-4, 5, 6, 7-tetrabromobenzimidazole), which has an $IC_{50}$ compared with TBB of just a tenth, at 0.14 μM. It constitutes one of the highest potency representatives of these halogenated benzimidazole derivatives (Pagano et al., 2004). In a further selectivity investigation, it was found that DMAT also inhibits other protein kinases, for example PIM 1 ("proto-oncogene serine/threonine-protein kinase 1") and DYRK1a ("dual-specificity tyrosine-phosphorylated and regulated kinase 1a"), with a similar potency (Sarno et al., 2003; Pagano et al., 2008), which boosts its significance as a selective CK2 inhibitor. For this reason, recently an increase in the selectivity of benzimidazole derivatives has primarily been sought (Pagano et al., 2008).

Several polyphenolic CK2 inhibitors can be isolated from plant extracts. A series of natural flavonoids such as apigenin (from *Apium graveolens*, FIG. 2), luteolin or quercetin even have $IC_{50}$ values of about 1 μM (Li et al., 2009), but at the same time inhibit other protein kinases, sometimes by significantly more than CK2. Haematin is much more selective, with an $IC_{50}$ of 0.55 μM (Hung et al., 2009). Some anthraquinone derivatives are CK2 inhibitors. A potent representative of this group is emodin from *Rheum palmatum* (FIG. 2), which has an $IC_{50}$ of about 1 μM with mediocre selectivity for CK2 (Yim et al., 1999). Both its potency and also its selectivity can be improved by modifications. Thus, MNX (1,8-dihydro-4-nitroxanthen-9-one) has an $IC_{50}$ of 0.4 μM and chinalizarin (1, 2, 5, 8-tetrahydroxyanthraquinone) has an $IC_{50}$ of 0.11 μM (Cozza et al., 2009). By modifying the basic framework to coumarin derivatives, further inhibitors can be developed which overcome some of the disadvantages of anthraquinone derivatives. A potent representative of these coumarin derivatives is DBC (3,8-dibromo-7-hydroxy-4-methyl-chromene) with an $IC_{50}$ of 0.1 μM. Ellagic acid (FIG. 2) has been identified as the most potent polyphenolic CK2 inhibitor from plant secondary metabolism so far. It has an $IC_{50}$ of 0.04 μM and exhibits selective inhibition of CK2 in comparison with 12 other protein kinases (Cozza et al., 2006).

In recent years, technical advances such as computer-based methods or library screening have meant that CK2 inhibitors have been identified with heretofore unknown basic frameworks. By way of examples, synthetic IQA (5-oxo-5,6-dihydroindolo[1,2-a]quinazolin-7-yl) acetic acid, FIG. 2, as well as ellagic acid, mentioned above, have been identified as CK2 inhibitors using computer-based virtual screening methods (Sarno et al., 2003). The indoloquinazoline derivative IQA is structurally different from all other described inhibitors, has an $IC_{50}$ of 0.39 μM and exhibits selective CK2 inhibition for 44 protein kinases (Santo et al., 2003). Thus, it is indeed less potent than other inhibitors, but exhibits better selectivity and allows further structural modifications. Further, TBCA (tetrabromocinnamic acid) has been identified, with a $IC_{50}$ of 0.11 μM and is selective for CK2 for 28 tested protein kinases (Pagano et al., 2007). Recently, planar, partly macrocyclic pyrazolo[1,5-a][1,3,5]triazines have been described, which have exhibited strongly inhibitory activity for CK2 in initial cell culture tests (Nie et al., 2008) and are currently undergoing further investigation. More recently, inhibition data has been obtained for substituted pyrazine frameworks. Derivatives of this class of substrates have in initial inhibition tests with CK2CK2 indicated values in the nanomolar region (Suzuki et al., 2008).

The co-substrate cavity is currently the target structure to which the most potent inhibitors of CK2 bind. The ATP concentration in the cell is in the range 1 mM to 10 mM (Cohen, 1999). Possible ATP competitive inhibits must exhibit a high affinity in order to force ATP from its binding cavity under these conditions. In addition, precisely this structure is varied the least in different protein kinases. Thus, it is difficult to develop selective ATP competitive inhibitors for CK2. Selective addressing of the target molecule is thus a prerequisite for potential clinical use. Furthermore, a pharmaceutical candidate should satisfy conventional requirements of medical chemistry, such as Lipinski's rule of five (Lipinski et al., 2001). It must be water-soluble, cell-permeable and stable under physiological conditions in order to ensure sufficient bioavailability.

A major disadvantage of many anthraquinone derivatives such as emodin is its potential intercalation into DNA (Wang et al., 2006). This property makes the substrate group unusable for CK2-specific investigations in cellular systems and for targeted therapeutic CK2 inhibition. TBB, on the other hand, is suitable for in vitro experiments but because of its relatively poor solubility in water, this CK2 inhibitor is not suitable for clinical use (Battistutta et al., 2000). IQA is also potent and highly selective for CK2, but is unstable in aqueous media since its lactam ring is prone to slow hydrolysis (Sarno et al., 2003; Sarno et al., 2005). As shown in these examples, until now only very few of published ATP-competitive CK2 inhibitors satisfy the basic requirements for a pharmaceutical candidate. This is also a reason for the development of inhibitors with alternative mechanisms, which are gaining significance. For DRB, by co-crystallization with CK2, it was noticed by chance that this compound in addition to an affinity for the co-substrate cavity, also has an affinity for a hydrophilic binding cavity on the contact surface with the β subunit. This binding cavity, as an allosteric target for new selective inhibitors, could inhibit tetramerization of CK2 and thus influence its regulation. Furthermore, in the last three years, various substances have been found which effectively prevent binding of CK2α and CK2β (Prudent et al., 2010). Thus, cyclic 11-mer peptides could be derived from CK2β which, in low micromolar concentrations, block the formation of the CK2α-CK2β complex (Laudet et al., 2007). Based on these results, the same group succeeded in developing low molecular weight substrates which address these allosteric binding cavities. They are podophyllotoxin-indolo derivatives which are non-competitive inhibitors with $IC_{50}$ values of up to 20 µM (Laudet et al., 2008). In addition, inorganic substances may act as allosteric inhibitors. As an example, for some polyoxometallates, $IC_{50}$ values in the single FIGURE nanomolar region both for CK2α and also for the holoenzyme were found (Prudent et al., 2008). In addition to the CK2α-CK2β contact, the acidophilic substrate binding site of CK2α offers a less frequently addressed, attractive structure for the development of selective inhibitors. In a seldom-cited study, a Cuban group reports on a cyclic peptide with an affinity for CK2α (amino acid sequence CWMSPRHLGTC) (Perea et al., 2004). The authors developed the fusion peptide CIGB-300, which consists of this sequence and a cell-permeable peptide derived from the HIV Tat protein. In vivo studies showed that CIGB-300 had pro-apoptotic potential and caused growth inhibition of tumour tissue (Perea et al., 2008). However, that study was silent as to whether the pro-apoptotic activity of CIGB-300 could actually be put down to an inhibition of CK2. More recent investigations no longer report a general inhibition of CK2 by CIGB-300 but an interaction between CIGB-300 and nucleophosmin, a CK2 substrate (Perera et al., 2009).

It can be assumed that in addition to the published research results, several industrial programmes are being run to develop CK2 inhibitors. As an example, it has only recently been discovered that with the substance CX-4945 (FIG. 2), the first low molecular weight CK2 inhibitor is being investigated in a clinical phase I study as an oral cancer drug (Chua et al., 2008; Pinna and Allende, 2009). In the pre-clinical investigation, CX-4945 exhibited potent and selective inhibition of CK2 as well as good anti-tumour properties in cell lines and xenograft cancer models (Dancey, 2009).

Substances which modulate the activity of CK2 constitute useful tools with which the (patho)physiological functions of this enzyme can be illuminated. In addition to the variation in available CK2 inhibitors, the announcement of new guide structures makes an important contribution to the development of potent and selective substances which are also suitable for clinical use. Initial successes reinforce the hope that CK2 inhibitors will be able to be identified which can be used as targeted pharmaceuticals in tumour therapy.

In view of the foregoing, then, the aim of the present invention is to provide novel compounds for the selective inhibition of protein kinases as well as a drug and/or pharmaceutical which comprises such novel compounds. Furthermore, the aim of the present invention is to provide a diagnostic tool for investigating the role of protein kinases, in particular serine/threonine kinases, in particular the protein kinase CK2, in cellular processes, the pathogenesis of diseases, ontogenesis and/or other developmental biological phenomena or interrelationships.

This aim is achieved, in respect of the compound and the drug or pharmaceutical, by means of a pharmaceutical preparation which is characterized in that it has, as the active ingredient, at least one compound with general formula I:

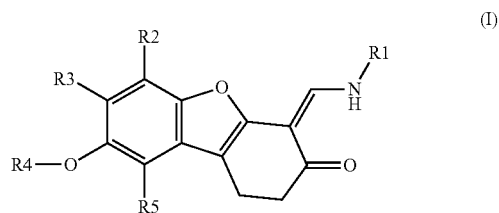

wherein R1 is a substituted or unsubstituted aryl group or a substituted or unsubstituted alkyl group containing 1 to 16 C atoms, preferably a halogen, alkoxy and/or alkyl-substituted aryl group; R2, R3 and R5 are independently F, Cl, Br, I, H, a hydroxyl group or an alkoxy group containing 1 to 4 C atoms; and R4 is H, an alkyl or acyl group containing 1 to 16 C atoms, preferably $(C_nH_{2n+1})$—CO, with n=1, 2, 3, 4, 5, 6, 7 or 8.

Surprisingly, it has been shown that dibenzofuranone derivatives in accordance with general formula I are capable of selectively inhibiting kinases, in particular serine/threonine kinases, and thus of initiating targeted apoptosis of neoplastic tissue.

In one embodiment of the invention, R1 is a para-substituted aryl group, R2 and R3 are independently F, Cl or H, R4 is H or $CH_3CO$, and R5 is H.

In a further embodiment of the pharmaceutical preparation of the invention, R1=4-$CH_3OC_6H_4$, 4-$CH_3C_6H_4$ or 4-$FC_6H_6$.

In a further, preferred embodiment, R1=4-$CH_3C_6H_4$; R2 and R3=Cl; and R4 and R5=H.

In a further, preferred embodiment, R1=4-$CH_3OC_6H_4$; R3 and R5=Cl; R2 and R4=H.

The pharmaceutical preparation of the invention may further contain pharmaceutically acceptable additives and auxiliary substances. Furthermore, they may comprise at least one further compound with an anti-neoplastic effect.

In respect of the diagnostic tool, the aim of the invention is achieved through the use of a compound with general formula I:

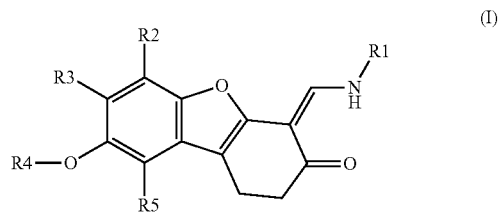

wherein R1 is a substituted or unsubstituted aryl group or a substituted or unsubstituted alkyl group containing 1 to 16 C atoms, preferably a halogen, alkoxy and/or alkyl-substituted aryl group; R2, R3 and R5 are independently F, Cl, Br, I, H, a hydroxyl group or an alkoxy group containing 1 to 4 C atoms; and R4 is H, an alkyl or acyl group containing 1 to 16 C atoms, preferably $(C_nH_{2n+1})$—CO, with n=1, 2, 3, 4, 5, 6, 7 or 8, as a diagnostic tool for the investigation of the role of protein kinases, in particular serine/threonine kinases, in particular the protein kinase CK2, in cellular processes, the pathogenesis of diseases, ontogenesis and/or other developmental biological phenomena or interrelationships.

Furthermore, it has been shown that compounds with general formula I:

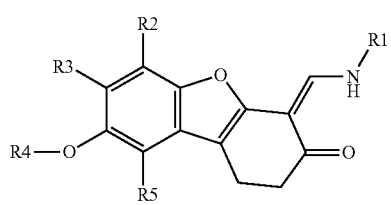

(I)

wherein R1 is a substituted or unsubstituted aryl group or a substituted or unsubstituted alkyl group containing 1 to 16 C atoms, preferably a halogen, alkoxy and/or alkyl-substituted aryl group; R2, R3 and R5 are independently F, Cl, Br, I, H, a hydroxyl group or an alkoxy group containing 1 to 4 C atoms; and R4 is H, an alkyl or acyl group containing 1 to 16 C atoms, preferably $(C_nH_{2n+1})$—CO, with n=1, 2, 3, 4, 5, 6, 7 or 8, exhibit antioxidative properties and thus can be used as an antioxidative substance for the production of pharmaceuticals, in particular for preventative use.

Furthermore, it has been shown that compounds with general formula II:

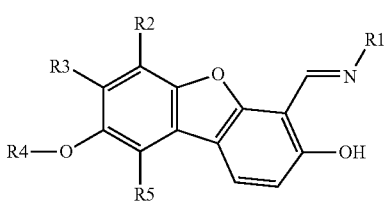

(II)

wherein R1 is a substituted or unsubstituted aryl group or a substituted or unsubstituted alkyl group containing 1 to 16 C atoms, preferably a halogen, alkoxy and/or alkyl-substituted aryl group; R2, R3 and R5 are independently F, Cl, Br, I, H, a hydroxyl group or an alkoxy group containing 1 to 4 C atoms; and R4 is H, an alkyl or acyl group containing 1 to 16 C atoms, preferably $(C_nH_{2n+1})$—CO, with n=1, 2, 3, 4, 5, 6, 7 or 8, can also be used as active ingredients in pharmaceutical preparations. In this regard, it has also, surprisingly, been shown that compounds in accordance with general formula II are capable of selectively inhibiting kinases, in particular serine/threonine kinases, and thus can introduce targeted apoptosis of neoplastic tissue.

In a preferred embodiment, in formula II, R1=4-$CH_3OC_6H_4$; R3 and R5=Cl; R2 and R4=H.

The invention will now be described in more detail with the aid of examples; the inventive concept is not, however, limited to these examples.

FIG. 4 shows the effect of TF (A) and TBB (B) on the viability of LNCaP cells;

Figure 10:
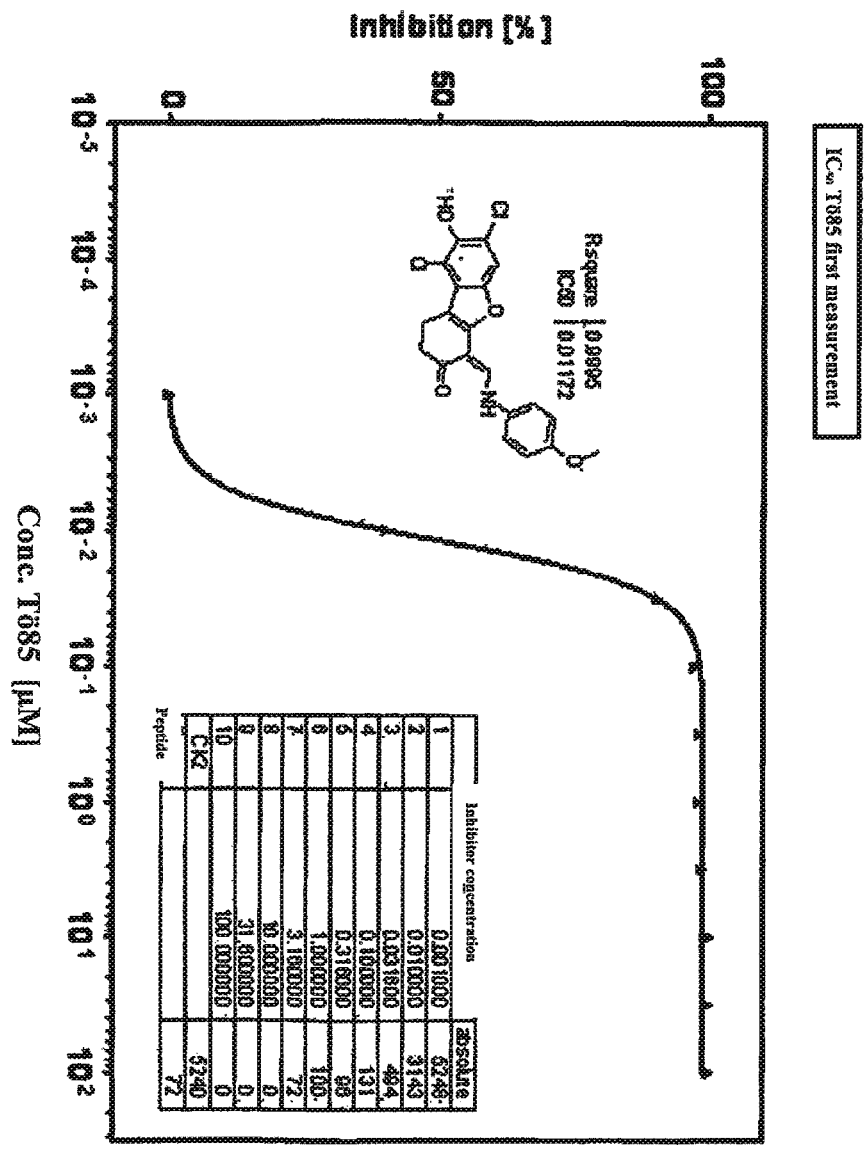
Figure 11:
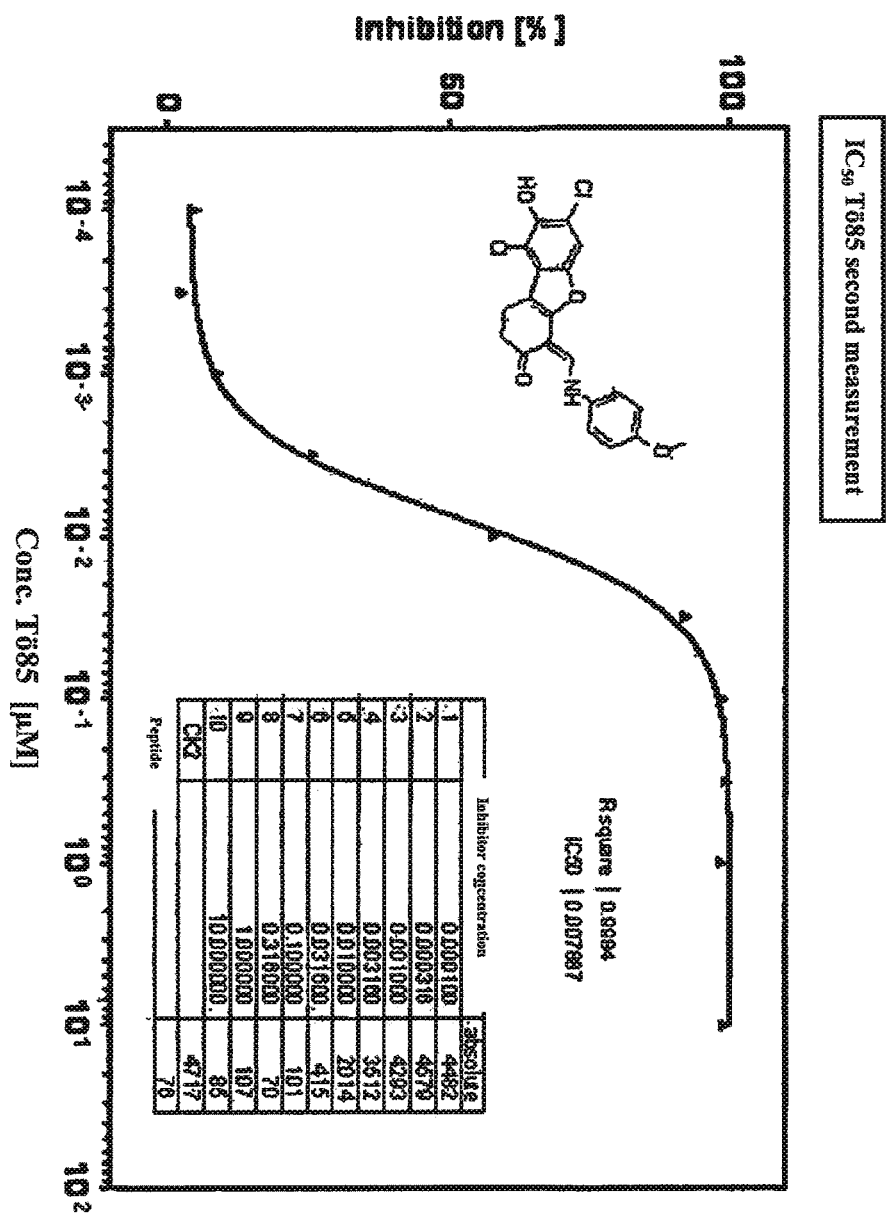
Figure 12:
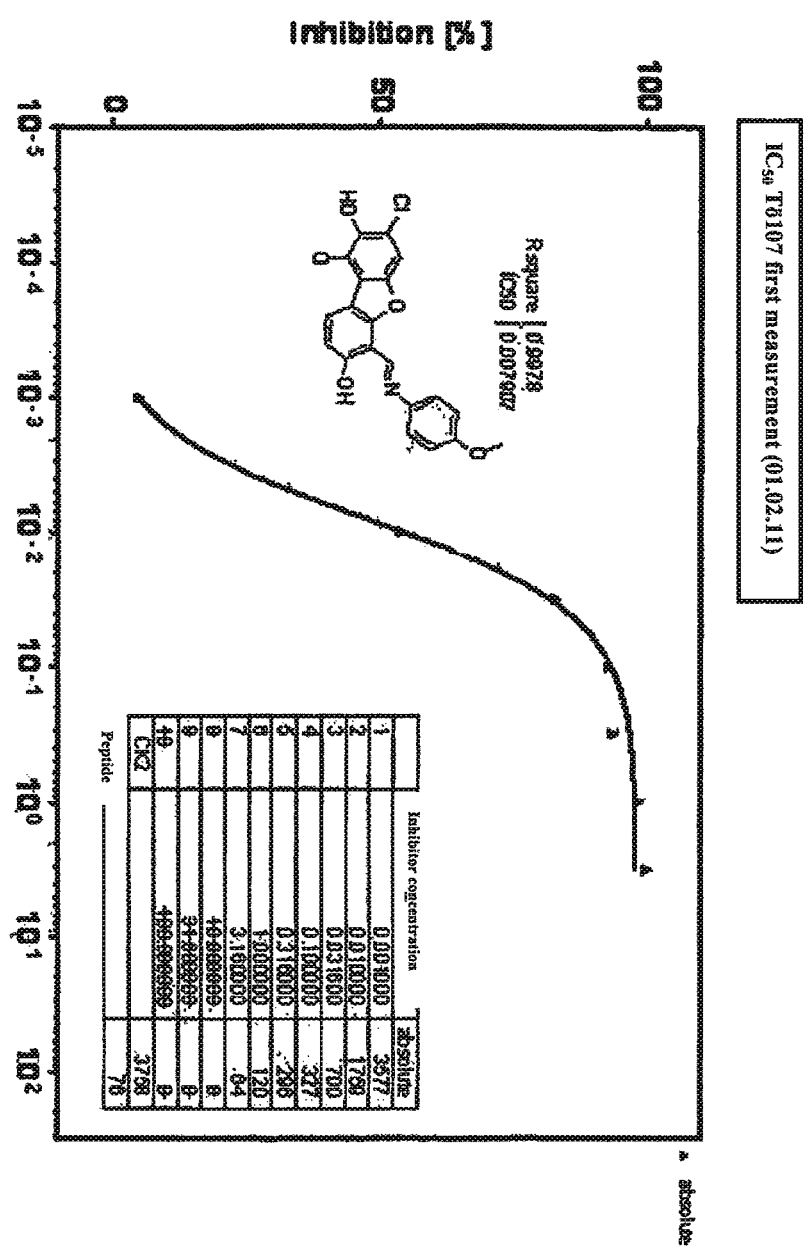
Figure 13:
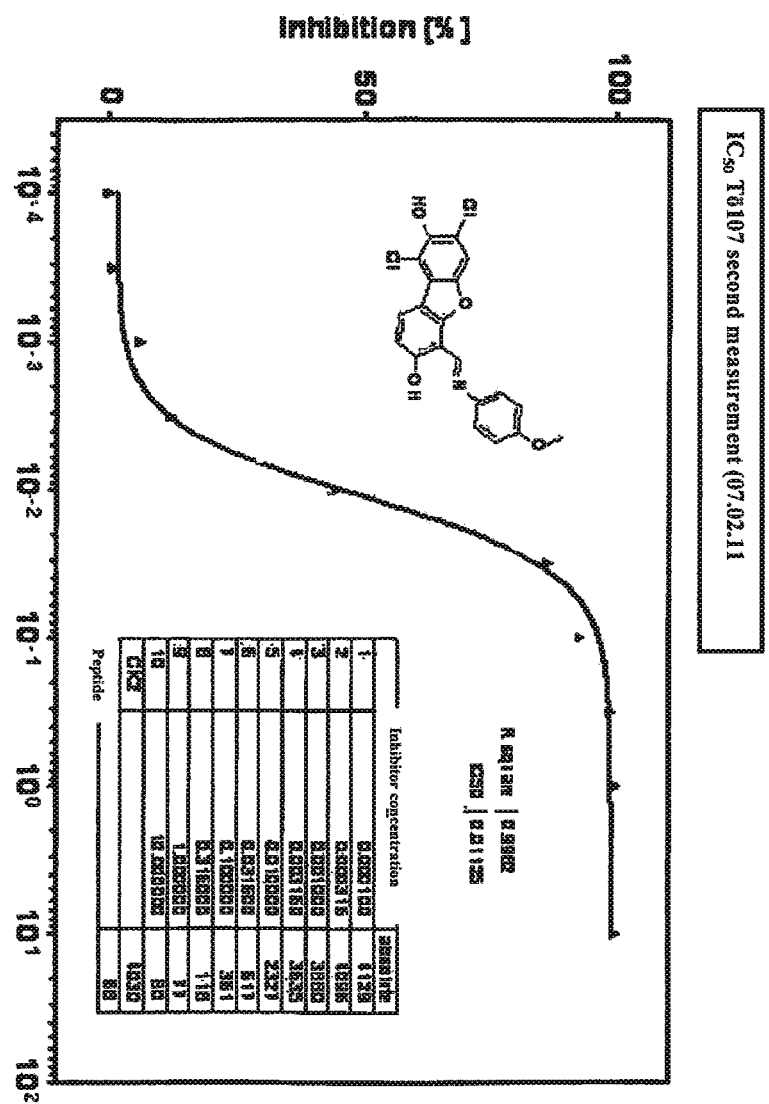
Figure 14:
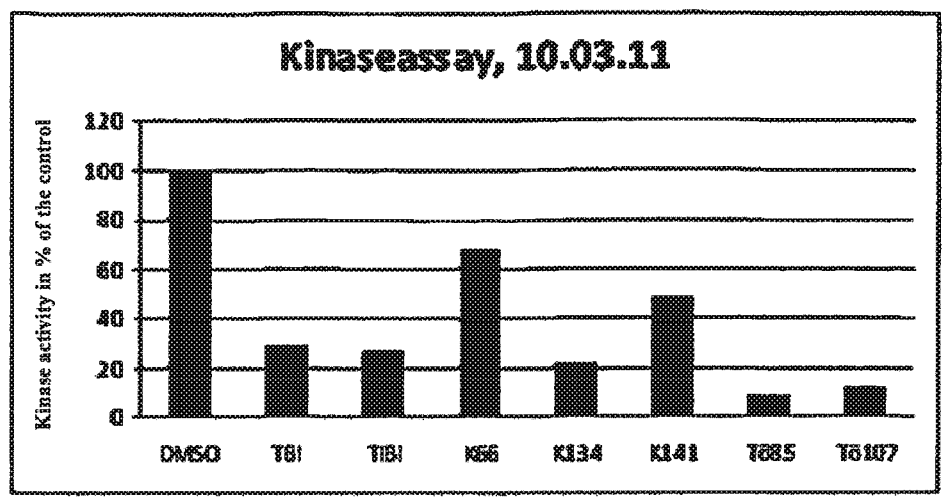
Figure 15:
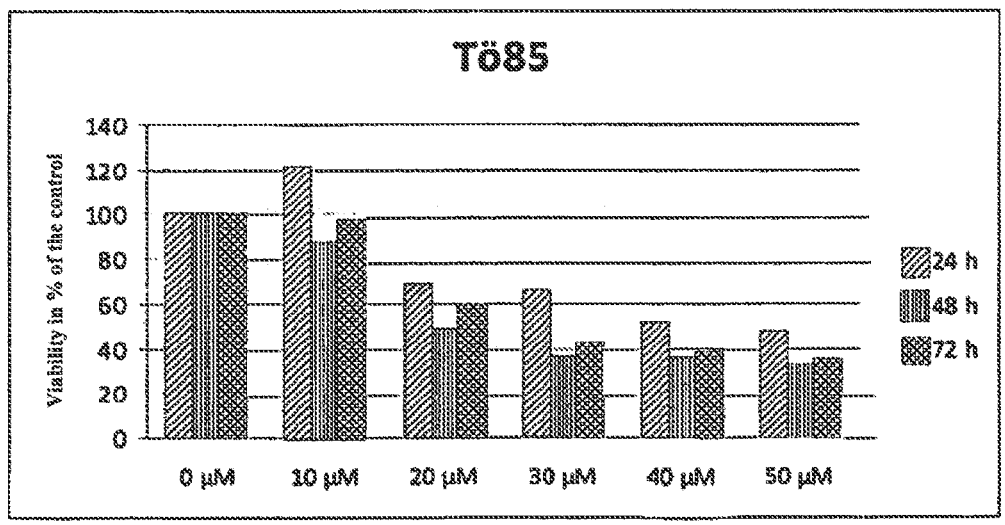
Figure 16:
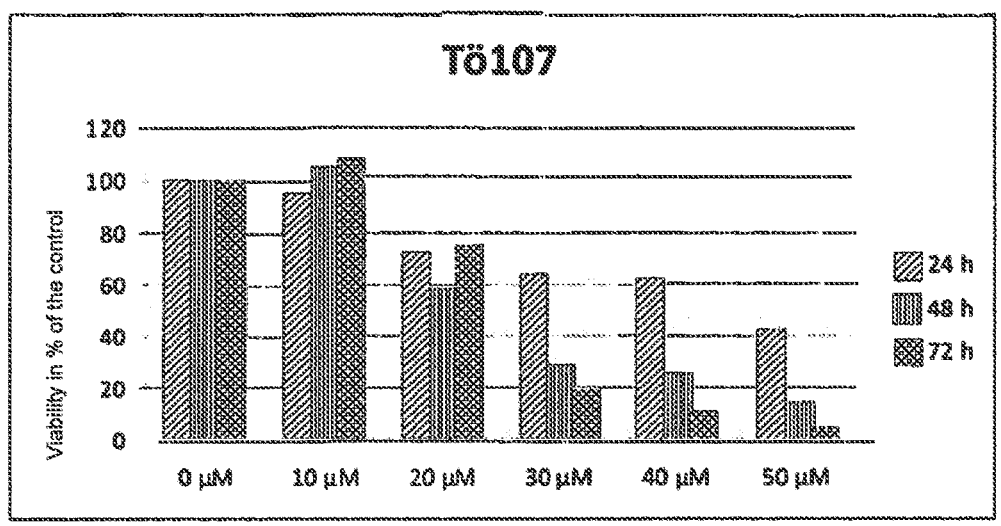

FIG. 10 shows a first determination of the $IC_{50}$ of the compound Tö85, in which in general formula I, the substituents are: R1=4-$CH_3OC_6H_4$; R3 and R5=Cl; R2 and R4=H;

FIG. 11 shows a second determination of the $IC_{50}$ of Tö85;

FIG. 12 shows a first determination of the $IC_{50}$ of compound Tö107, in which in general formula II, the substituents are: R1=4-$CH_3OC_6H_4$; R3 and R5=Cl; R2 and R4=H;

FIG. 13 shows a second determination of the $IC_{50}$ of Tö107;

FIG. 14 shows the inhibition of the protein kinase CK2 in cells of the prostate cancer cell line LNCaP by Tö85 and Tö107 compared with the compounds DMSO, TBI, TIBI, K66, K134 and K131;

FIG. 15 shows the concentration-dependent reduction in the viability of cells of the prostate cancer cell line LNCaP by Tö85;

FIG. 16 shows the concentration-dependent reduction in the viability of cells of the prostate cancer cell line LNCaP by Tö107.

Figure 1:
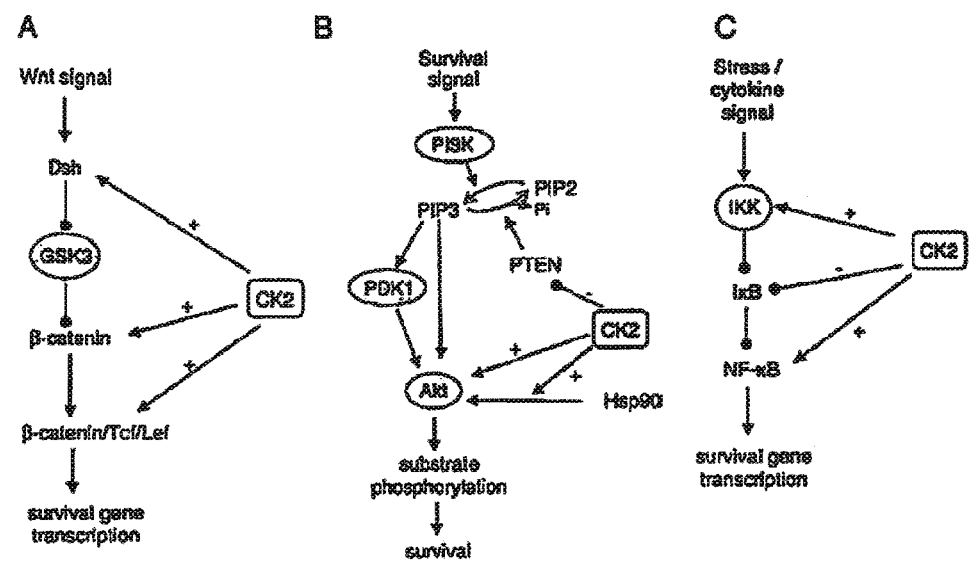
FIG. 1 shows the lateral effect of CK2 on (A) Wnt-, (B) Akt-, and (C) NF-κB-signal transduction.

FIG. 1 shows the lateral effect of CK2 on (A) Wnt-, (B) Akt-, and (C) NF-κB-significant transduction. Negative effects (−) are shown by pinhead arrows and are based on the inhibition of or reinforcement of degradation. Positive effects (+) are shown by normal arrows and are based on reinforced stability and/or activity (modified in accordance with Ruzzene and Pinna (2010)).

Figure 2:
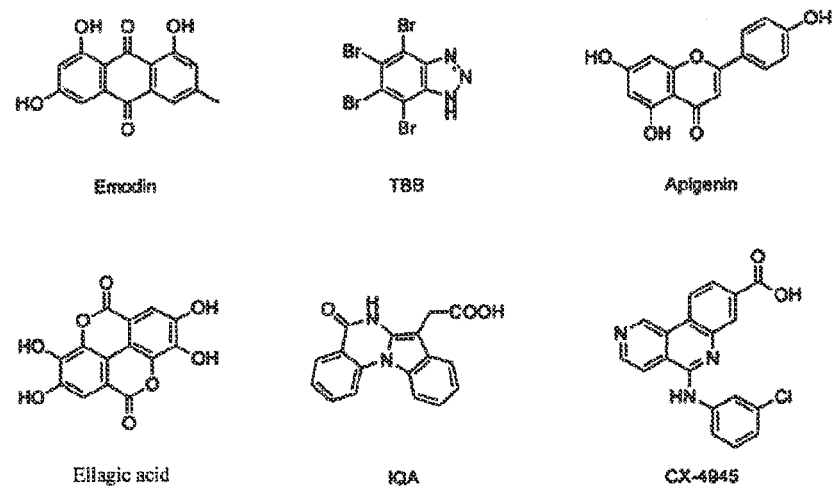
FIG. 2 shows examples of ATP-competitive inhibitors with different basic frameworks which affect the activity of CK2 even in micromolar concentrations.

FIG. 2 shows examples of ATP-competitive inhibitors with different basic frameworks from the prior art which have an effect on the activity of CK2 even in micromolar concentrations.

Figure 3:
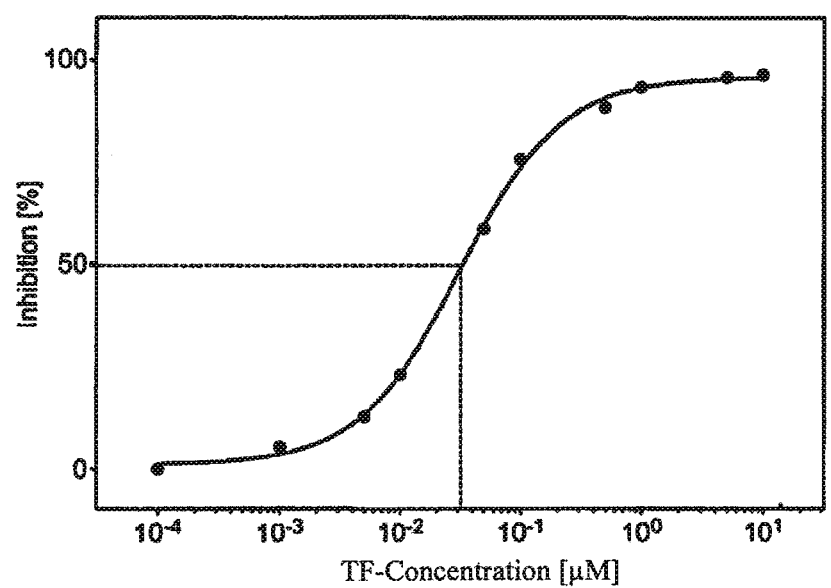
FIG. 3 shows the determination of the $IC_{50}$ of TF.

FIG. 3 shows the determination of the $IC_{50}$ of TF. To this end, the capillary electrophoretic CK2 inhibition test using E-peptide as the substrate was carried out. The inhibition of CK2 was measured after ten minutes of pre-incubation with TF. Ten concentrations between 0.0001 μM and 10 μM were investigated for this purpose.

FIG. 4 shows the effect of TF (A) and TBB (B) on the viability of LNCaP cells. The viability was determined with the aid of the MTT test. Each diagram shows the concentration-dependent effect after an incubation period of 24 h (●), 48 h (□) and 72 h (▲).

Figure 5:
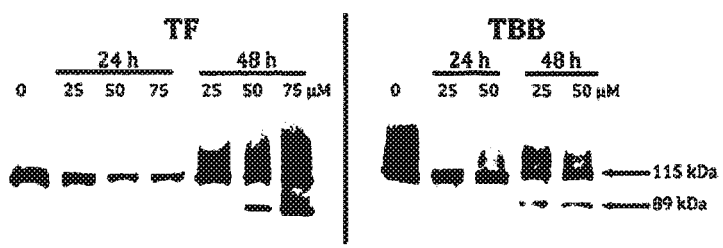
FIG. 5 shows the effect of TF and TBB on PARP cleavage in LNCaP cells.

FIG. 5 shows the effect of TF and TBB on PARP cleavage in LNCaP cells. The cells were incubated for 24 h or 48 h with 25 μM, 50 μM and 75 μM TF or with 25 μM, 50 μM TBB. The controls were cells which had only been treated with DMSO (0 μM). After SDS-PAGE and Western Blotting, complete PARP (115 kDa) and the 89 kDa fragment obtained after caspase cleavage with the aid of an anti-PARP antibody were labelled.

Figure 6:
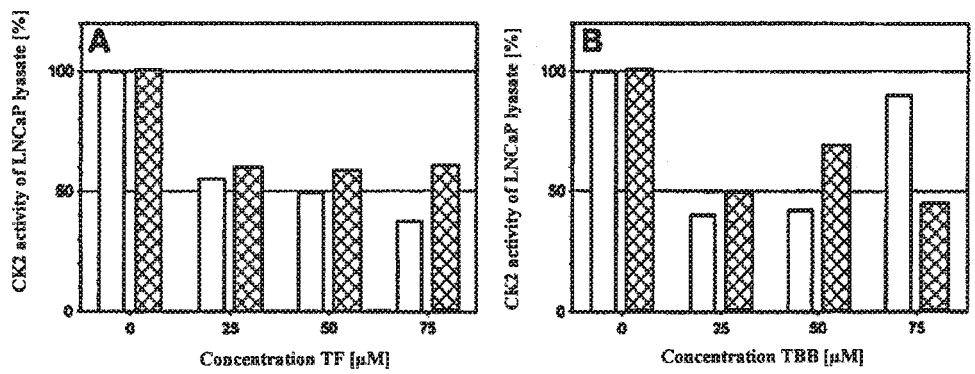
FIG. 6 shows the CK2 activity in lysates of LNCaP cells which have been incubated with TF (A) or TBB (B)

FIG. 6 shows the CK2 activity in lysates from LNCaP cells, which had been incubated with TF (A) or TBB (B). The CK2 activity was determined using a radiometric test procedure. The relative activities of the samples were each relative to untreated cells. White bars show the CK2 activity after 24 h; grey bars show the CK2 activity after 48 h incubation with each inhibitor. For samples (A) treated with TF, double determinations were carried out (the mean value is given in each case).

Figure 7:
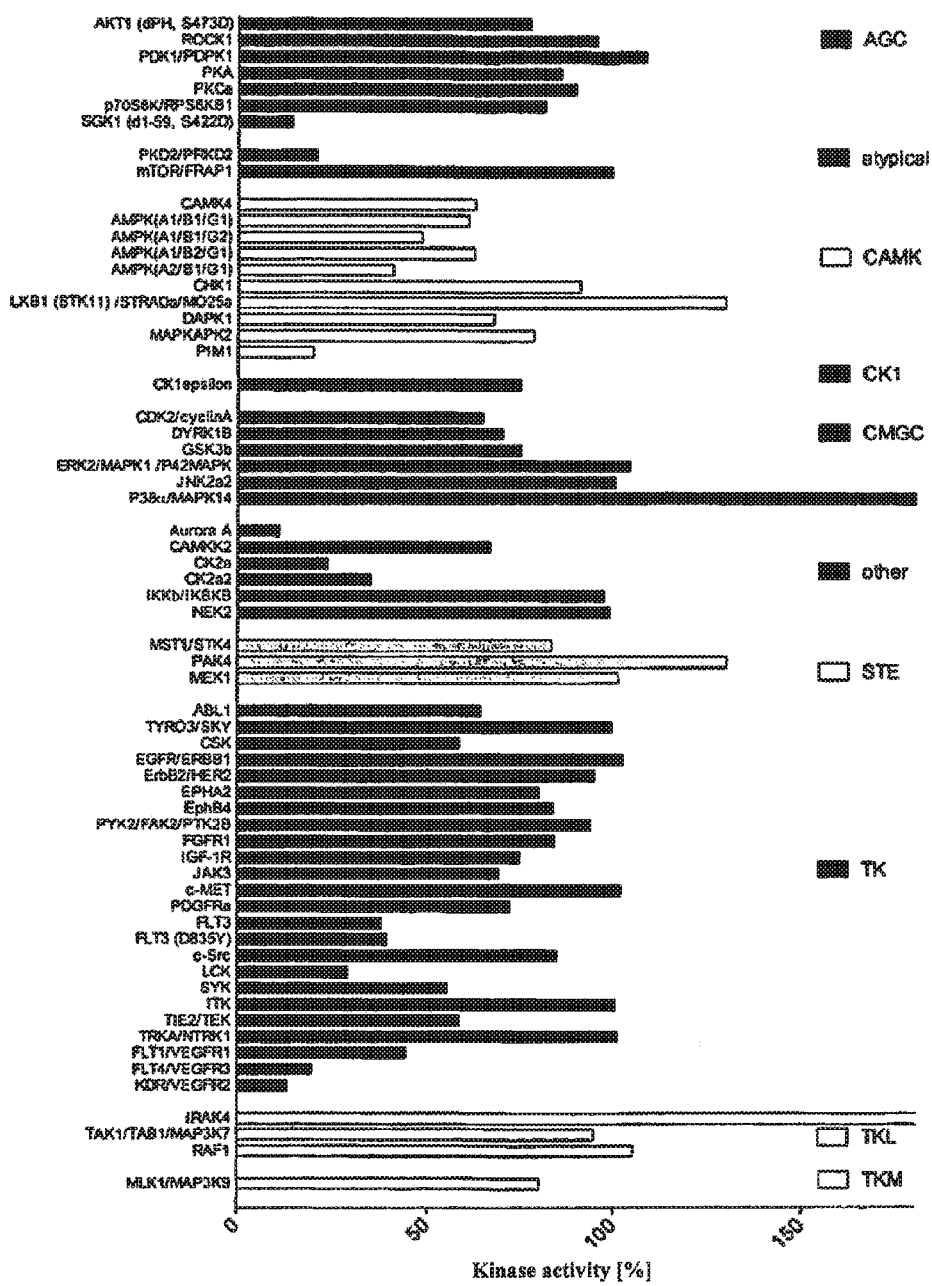
FIG. 7 shows the selectivity profile of with a selection of 63 human protein kinases.

FIG. 7 shows the selectivity profile of TF with a selection of 63 human protein kinases. The listed PKs were incubated with 10 µM TF and 10 µM ATP. Next, the relative percentage kinase activity was determined (mean value from n=2). 100% activity was defined as the activity of the respective kinase in the absence of TF. The PK grouping was in accordance with Manning et al. (2002).

Figure 8:
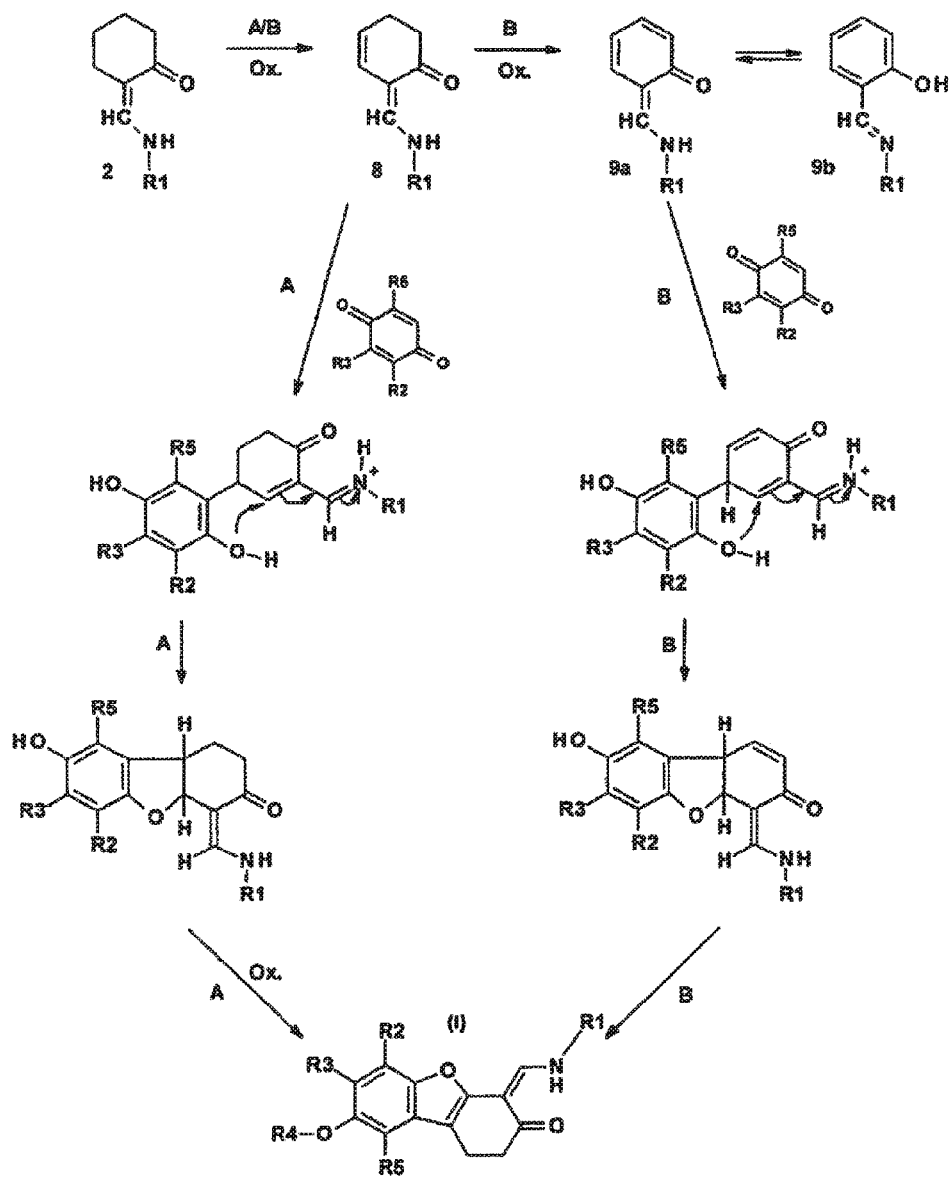
FIG. 8 shows the synthesis scheme for the synthesis of compounds with general formula I.

Compounds with general formula I can be obtained in accordance with the synthesis scheme shown in FIG. 8 from suitable 1,4-benzoquinone derivatives by reaction with appropriate (aminomethylene)cyclohexanone derivatives. When forming the compounds of the invention with general formula I, both reaction pathways A and B can in principle be followed. Because of the high oxidizing power of the chlorinated quinones 1a and b, in contrast to the simple 1,4-benzoquinone or 2-methyl-1,4-benzoquinone, dehydration of the enaminone 2 occurs prior to addition. The yield of dibenzofuranone with general formula I can be successively increased by increasing the quantity of quinone from 10% to 20%.

Following the identification of Ric152 as a potent CK2-Inhibitor, further benzofuran derivatives were provided by Prof. Kuckländer (Kuckländer and Töberich, 1982; Bollig, 2007). The effect of these substances on CK2 activity was initially investigated at a concentration of 10 µM, once again. At an inhibition of CK2 activity of >50%, the $IC_{50}$ of the substance was also determined in order to quantify the inhibitory potential more accurately. The results obtained for the investigated substances from the capillary electrophoretic test procedure are summarized in Table 2.

Figure 9:
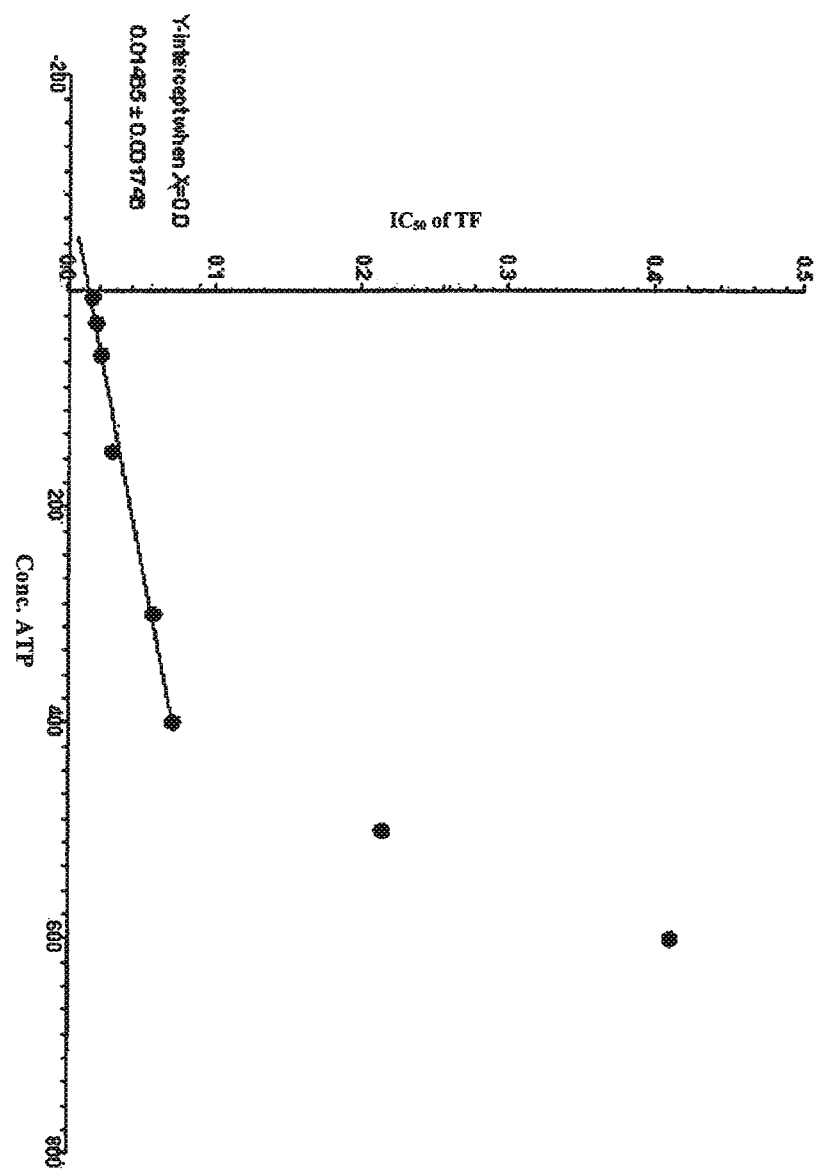
FIG. 9 shows the investigation of the mode of inhibition of the compound TF.

FIG. 9 shows the investigation of the mode of inhibition of the compound TF. To this end, $IC_{50}$ values for TF were determined for 8 different ATP concentrations. An increase in the $IC_{50}$ with increasing ATP concentration indicates that TF is an ATP competitive inhibitor. From these data, the inhibition constant $K_i$ could also be obtained. This can be read from FIG. 9 as the intersection of the best-fit line of the linear region with the Y axis. The $K_i$ obtained in this manner for TF is 14.65 nM±1.75 nM).

TABLE 2

Investigation of various benzofuran derivatives on the inhibition of CK2 in the capillary electrophoretic activity test

| Substance | Structural formula | CK2-activity at 10 µM | $IC_{50}$ |
|---|---|---|---|
| TF | | <4%[1] | 0.03 µM |
| Ric151 | | <4%[1] | 0.2 µM |
| Ric152 | | 7% | 0.2 µM |
| Ric138 | | 31% | 2.4 µM |

TABLE 2-continued

Investigation of various benzofuran derivatives on the
inhibition of CK2 in the capillary electrophoretic activity test

| Substance | Structural formula | CK2-activity at 10 μM | IC$_{50}$ |
|---|---|---|---|
| Ric149 | 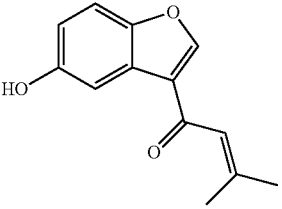 [SMILES: CC(C)=CC(=O)c1coc2ccc(O)cc12] | 61% | — |
| RicFur | 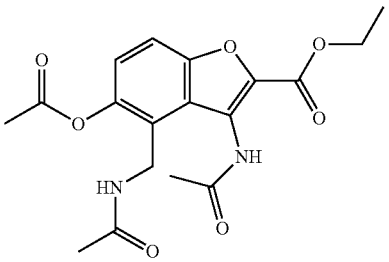 [SMILES: CCOC(=O)c1oc2ccc(OC(C)=O)c(CNC(C)=O)c2c1NC(C)=O] | 110% | — |

[1]Values below 4% could no longer be reliably quantified.

The investigated benzofuran derivatives exhibited clear differences in CK2 inhibition. Ric149 and RicFur exhibited a low or even zero inhibiting effect on CK2 activity. In contrast, the inhibition effect of TF, Ric151, Ric152, Ric138 resulted in a CK2 residual activity of less than 50%. For these substances, IC$_{50}$ values were also determined. On closer inspection, for substances Ric138 and Ric152, an interesting structure-effect relationship was observed. They only differ in the side chain in position 2 of the benzofuran ring. This structural difference is reflected in a 10-fold difference in IC$_{50}$, which for Ric138 is 2.4 μM and for Ric152 is 0.2 μM. Exchanging the ethyl ester functionality of Ric138 for the α,β-unsaturated carbonyl system (3-methylbutenone) of Ric152 appears to have a positive effect on the inhibitory potential. Acetylation of the phenolic hydroxyl group in position 5 of the benzofuran ring appears not to be essential for the effect of Ric152, since the correspondingly deacetylated derivative Ric151 has an identical IC$_{50}$ of 0.2 μM, the best IC$_{50}$ is provided by "Töberichfuran", (Z)-6,7-dichloro-1,4-dihydro-8-hydroxy-4-[(4-methylphenylamino)methylene]-dibenzo[b,d]furan-3(2H)-one, abbreviated to TF (Kuckländer and Töberich, 1982). At 0.03 μM, this was very nearly one tenth of the IC$_{50}$ of Ric151 and Ric152 (FIG. 3).

TF was identified as an extremely potent CK2 inhibitor and was investigated as regards its membrane accessibility, growth-inhibiting properties and inhibition of native CK2 in the human prostate cancer cell line LNCaP (Horoszewicz et al., 1980). All of the cell culture experiments were carried out by Claudia Götz in Prof. Montenarh's group (Medizinische Biochemie and Molekularbiologie, Universitätskliniken des Saarlandes, Homburg/Saar [Medical Biochemistry and Molecular Biology, Clinical University of Saarland, Homburg/Saar]).

A MTT test was used to determine the effect of TF on the viability of LNCaP cells. To this end, these cell lines were treated with three concentrations of TF (25 μM, 50 μM, 75 μM). The effect was determined after 24 h, 48 h and 72 h as the relative viability compared with untreated cells. Analogously, LNCaP cells were incubated with the same concentrations of TBB inhibitor in order to compare the results under the same experimental conditions. After treating the LNCaP cells with TF, both the effects of increasing the concentration and also of prolonging the incubation time could be recorded. After 24 hours incubation with 25 μM of TF, the viability had already dropped to 45% and after the same incubation time with 50 μM of TF, it had dropped further to 30%. Incubation with 75 μM of TF, however, resulted in no further reduction (31% viability). The effects after 24 h could be reinforced in each case by extending the incubation time. Thus, after 48 hours incubation with 25 μM, 50 μM and 75 μM of TF, a viability of 37%, 15% or 12% was observed. After 72 hours incubation with a fixed time concentration of 25 μM, a viability of only 14% could be detected, which dropped to 5% and 3% respectively for higher TF concentrations of 50 μM and 75 μM (FIG. 4A). Treating LNCaP cells with TBB had a similar effect, but only at higher concentrations, or longer incubation times. Thus, an incubation time of 24 h had only a small effect. With the maximum TBB concentration of 75 μM, a viability of 90% was measured after 24 h. Even after 72 h, at the lowest TBB concentration of 25 μM, no effects were observed. Only at the highest concentration of 75 μM, a reduction to 45% after 48 h was recorded, and after 72 h, the viability was still 17% (FIG. 5B). Considering the respective incubation times, the effects of the highest TBB concentrations investigated (75 μM) were already exceeded by the lowest investigated TF concentration (25 μM). In summary, it has been shown that the viability of LNCaP cells is reduced by both substances. The newly identified CK2 inhibitor TF, however, is far more potent than the known inhibitor TBB.

Next, we investigated whether the TF-mediated reduction in cell viability could be related to apoptotic events. To this end, cleavage of poly(ADP-ribose)-polymerase (PARP) in cells was assayed. Caspase 3 cleaves the 115 kDa PARP into two stable fragments: the 24 kDa DNA-binding N-terminal domain and the 89 kDa C-terminal fragment. This specific proteolysis of PARP characterizes the irreversible point of initiation apoptosis and can be assayed in a Western Blot of cell lysates with a specific PARP antibody. LNCaP cells were investigated for PARP cleavage after 24 and 48 hour incubation with 25 μM, 50 μM and 75 μM of TF and compared with the effect of TBB at the same concentration. After incubation with TF, from 50 μM, it was observed that the bands of the 89 kDa PARP fragment increased in intensity in a concentration-dependent manner. This effect was observed both after an incubation time of 24 h and also, more strongly, after 48 h. A treatment of the LNCaP cells with TBB in these experiments produced almost identical results (FIG. 6). In this case, even at a concentration of 25 μM, a faint band could be seen at 89 kDa. LNCaP cells which were incubated with 75 μM of TBB could not be evaluated because of technical difficulties. As a result, it can be seen that both TF and TBB have a similar strong pro-apoptotic effect in LNCaP cells in the concentration range being investigated.

LNCaP cells were incubated with TF in the same manner as in the experiments described above. After 24 h or 48 h, the CK2 activity of lysates was measured using radiometric CK2 testing. This investigation provided an indication as to whether the inhibition of TF found with the isolated enzyme could be observed in cellular systems. The influence of the respectively identical concentration of TBB on the inhibition of cellular CK2 activity acted as a comparison. Cells were incubated for 24 h or 48 h with 25 μM, 50 μM or 75 μM of TF and then washed and lysed. The relative CK2 activity was calculated from these cell lysates. The reference was the CK2 activity of cell lysates from untreated cells incubated for corresponding periods. In order to compensate for any fluctuations in the radiometric test, in the case of TF, two samples per parameter were measured. As a qualitative control, the TBB samples were used and measured individually. From a concentration of 25 μM, both substances resulted in a reduction in the endogenous CK2 activity of LNCaP cells to 50%. Increasing the concentration did not in any case result in a further reduction in the CK2 activity (FIG. 6).

In contrast to the MTT test, none of the tests showed up a link between extended incubation time with the appropriate substance and an increased inhibition of the endogenous CK2 activity. At the same time as the activity test, Western Blots were used to show that the expressed quantity of endogenous CK2α was not reduced in any of the cell lysates. The observed reduction in CK2 activity was thus due to modulation of the CK2 enzyme activity. Because of deviations in the radiometric test and the small number of equal samples, however, these results should primarily be considered to be a qualitative investigation. Thus, for example, the 24 h, 75 μM TBB incubated LNCaP cells with a CK2 activity of 90% was most probably a rogue result. Altogether, it can be seen that TF reduces the endogenous CK2 activity in LNCaP cells. The effect of TF was approximately the same as that of TBB. Proof of the inhibition of intracellular CK2 is provided by the ability of TF to permeate cells.

After the inhibitory potency of TF had been able to be established in LNCaP cells, the possibility that TF could be a selective CK2 inhibitor had to be investigated. To this end, the inhibiting effect of TF on 63 isolated human protein kinases (PK) was investigated by the firm "Reaction Biology" (Malvern, Pa., USA). These included representatives of PKs from all main groups of the human kinome (Manning et al., 2002). The results of this investigation are shown in FIG. 8, classified into the main human PK groups. In this series of tests, all of the PKs were each incubated with 10 μM of ATP and 10 μM of TF. In a subsequent radiometric test, the respective kinase activity with respect to a sample without TF was determined. Since the $K_M$ values of PK with respect to ATP occasionally differed substantially (Knight and Shokat, 2005), the results only allow a semi-quantitative comparison of inhibition by TF to be made. In this test, inhibition was defined as a reduction in activity of >50%, and so in addition to CK2α and CK2α', twelve of the 63 PK were inhibited by TF and 49 of the 63 PKs reacted weakly, not at all or in the case of IRAK4, MAPK14, PAK4 or LBK1, exhibited a clear increase in activity. CK2α (described in "Reaction Biology" as "CK2a") and CK2α' (described in "Reaction Biology" as "CK2a2") in this test were more weakly inhibited with just 24% or 35% residual activity (FIG. 7), as shown by the capillary electrophoretic inhibition investigation with the purified CK2 holoenzyme (<4% residual activity, Table 2). However, the different test parameters, such as substrate and ATP concentration, buffer, etc., must be taken into account and so a direct comparison of the inhibition data as a percentage is not possible at this point. The seven PKs which were inhibited the most strongly (>70%) are listed separately in Table 3. Although these results provide only a coarse overview of the quantitative inhibitory potential of TF, they indicate that TF is a multi-selective protein kinase inhibitor.

TABLE 3

Human protein kinases which are at least 30% inhibited by TF.

| Protein kinase | Activity | UniProt Accession # | Physiological function |
| --- | --- | --- | --- |
| Aurora A | 11.00% | O14965 | Cell cycle regulation |
| KDR/VEGFR2 | 13.05% | P35968 | Vessel development, angiogenesis |
| SGK1 (d1-59, S422D) | 14.16% | O00141 | Stress response, cell survival |
| FLT4/VEGFR3 | 19.68% | P35916 | Cell proliferation |
| PIM1 | 19.90% | P11309 | Cell proliferation, cell survival |
| PKD2/PRKD2 | 20.90% | Q9BZL6 | Resistance against oxidative stress |
| LCK | 29.20% | P06239 | T-cell differentiation |

BIBLIOGRAPHY

Ahmad, K. A., Wang, G., Unger, G., Slaton, J. and Ahmed, K. (2008) Protein kinase CK2-a key suppressor of apoptosis. *Adv Enzyme Regul* 48:179-87.

Ahmed, K., Issinger, O.-G., R. Marshak, D. and Pyerin, W. (1994) Editorial. *Cell Mol Biol Res* 40:371-2.

Allende, J. E. and Allende, C. C. (1995) Protein kinase CK2: an enzyme with multiple substrates and a puzzling regulation. *FASEB J* 9:313-23.

Allende-Vega, N., Dias, S., Milne, D. and Meek, D. (2005) Phosphorylation of the acidic domain of Mdm2 by protein kinase CK2. *Mol Cell Biochem* 274:85-90.

Augustine, S. A. J., Kleshchenko, Y. Y., Nde, P. N., Pratap, S., Ager, E. A., Burns, J. M., Lima, M. F. and Villalta, F. (2006) Molecular cloning of a *Trypanosoma cruzi* cell surface casein kinase II substrate, Tc-1, involved in cellular infection. *Infect Immun* 74:3922-9.

Barz, T., Ackermann, K., Dubois, G., Eils, R. and Pyerin, W. (2003) Genome-wide expression screens indicate a global role for protein kinase CK2 in chromatin remodeling. *J Cell Sci* 116:1563-77.

Battistutta, R. (2009) Protein kinase CK2 in health and disease: Structural bases of protein kinase CK2 inhibition. *Cell Mol Life Sci* 66:1868-89.

Battistutta, R., Sarno, S., De Moliner, E., Papinutto, E., Zanotti, G. and Pinna, L. A. (2000) The replacement of ATP by the competitive inhibitor emodin induces conformational modifications in the catalytic site of protein kinase CK2. *J Biol Chem* 275:29618-22.

Bibby, A. C. and Litchfield, D. W. (2005) The multiple personalities of the regulatory subunit of protein kinase CK2: CK2 dependent and CK2 independent roles reveal a secret identity for CK2beta. *Int J Biol Sci* 1:67-79.

Blanquet, P. R. (2000) Casein kinase 2 as a potentially important enzyme in the nervous system. *Prog Neurobiol* 60:211-46.

Blume-Jensen, P. and Hunter, T. (2001) Oncogenic kinase signalling. *Nature* 411:355-65.

Bollig, R. (2007) Neue cytostatisch wirksame Reaktionsprodukte der erweiterten Nenitzescu-Reaktion. Dissertation, Heinrich-Heine-Universität, Dússeldorf.

Bortolato, A., Cozza, G. and Moro, S. (2008) Protein kinase CK2 inhibitors: emerging anticancer therapeutic agents? *Anti-Cancer Agents Med Chem* 8:798-806.

Bretner, M., Najda-Bernatowicz, A., Lebska, M., Muszyńska, G., Kilanowicz, A. and Sapota, A. (2008) New inhibitors of protein kinase CK2, analogues of benzimidazole and benzotriazole. *Mol Cell Biochem* 316:87-9.

Brown, C. J., Lain, S., Verma, C. S., Fersht, A. R. and Lane, D. P. (2009) Awakening guardian angels: drugging the p53 pathway. *Nat Rev Cancer* 9:862-73.

Buchou, T., Vernet, M., Blond, O., Jensen, H. H., Pointu, H., Olsen, B. B., Cochet, C., Issinger, O.-G. and Boldyreff. B. (2003) Disruption of the regulatory beta subunit of protein kinase CK2 in mice leads to a cell-autonomous defect and early embryonic lethality. *Mol Cell Biol* 23:908-15.

Burnett, G. and Kennedy, E. P. (1954) The enzymatic phosphorylation of proteins. *J Biol Chem* 211:969-80.

Caples, M. J., Clements, J. E. and Barber, S. A. (2006) Protein kinase CK2 phosphorylates the Nef protein from a neurovirulent simian immunodeficiency virus. *Virology* 348: 156-64.

Carpenter, G., King, L. and Cohen, S. (1979) Rapid enhancement of protein phosphorylation in A-431 cell membrane preparations by epidermal growth factor. *J Biol Chem* 254: 4884-91.

Chalhoub, N. and Baker, S. J. (2009) PTEN and the PI3-kinase pathway in cancer. *Annu Rev Pathol* 4:127-50.

Cheek, S., Ginalski, K., Zhang, H. and Grishin, N. V. (2005) A comprehensive update of the sequence and structure classification of kinases. *BMC Struct Biol* 5:6.

Cheek, S., Zhang, H. and Grishin, N. V. (2002) Sequence and structure classification of kinases. *J Mol Biol* 320:855-81.

Chen, J., Gao, C., Shi, Q., Wang, G., Lei, Y.-J., Shan, B., Zhang, B., Dong, C., Shi, S., Wang, X., Tian, C., Han, J. and Dong, X.-P. (2008) Casein kinase II interacts with prion protein in vitro and forms complex with native prion protein in vivo. *Acta Biochim Biophys Sin (Shanghai)* 40:1039-47.

Chien, W. M., Parker, J. N., Schmidt-Grimminger, D. C., Broker, T. R. and Chow, L. T. (2000) Casein kinase II phosphorylation of the human papillomavirus-18 E7 protein is critical for promoting S-phase entry. *Cell Growth Differ* 11:425-35.

Chua, P., Pierre, F. and Whitten, J. P. (2008) Serine-threonine protein kinase and PARP modulators. Internationtional Patent Number: WO 2008/028168

Cohen, P. (1999) The development and therapeutic potential of protein kinase inhibitors. *Curr Opin Chem Biol* 3:459-65.

Cohen, P. (2002a) The origins of protein phosphorylation. *Nat Cell Biol* 4:E 127-30.

Cohen, P. (2002b) Protein kinases—the major drug targets of the twenty-first century? *Nat Rev Drug Discov* 1:309-15.

Cozza, G., Bonvini, P., Zorzi, E., Poletto, G., Pagano, M. A., Sarno, S., Donella-Deana, A., Zagotto, G., Rosolen, A., Pinna, L. A., Meggio, F. and Moro, S. (2006) Identification of ellagic acid as potent inhibitor of protein kinase CK2: a successful example of a virtual screening application. *J Med Chem* 49:2363-6.

Cozza, G., Bortolato, A. and Moro, S. (2010) How druggable is protein kinase CK2? *Med Res Rev* 30:419-62.

Cozza, G., Mazzorana, M., Papinutto, E., Bain, J., Elliott, M., di Maira, G., Gianoncelli, A., Pagano, M. A., Sarno, S., Ruzzene, M., Battistutta, R., Meggio, F., Moro, S., Zagotto, G. and Pinna, L. A. (2009) Quinalizarin as a potent, selective and cell-permeable inhibitor of protein kinase CK2. *Biochem J* 421:387-95.

Dancey, J. E. (2009) Kinase inhibitor 4 minisymposium summary. *Expert Rev Anticancer Ther* 9:891-4.

Daya-Makin, M., Sanghera, J. S., Mogentale, T. L., Lipp, M., Parchomchuk, J., Hogg, J. C. and Pelech, S. L. (1994) Activation of a tumor-associated protein kinase (p40TAK) and casein kinase 2 in human squamous cell carcinomas and adenocarcinomas of the lung. *Cancer Res* 54:2262-8.

Deana, A. D., Meggio, F., Pinna, L. A. and Moret, V. (1978) Different susceptibility of whole casein components to enzymatic phosphorylation by two forms of rat liver 'casein kinase'. *Biochim Biophys Acta* 524:316-26.

Delorme, V., Cayla, X., Faure, G., Garcia, A. and Tardieux, I. (2003) Actin dynamics is controlled by a casein kinase II and phosphatase 2C interplay on Toxoplasma gondii Toxofilin. *Mol Biol Cell* 14:1900-12.

DePaoli-Roach, A. A., Roach, P. J., Pham, K., Kramer, G. and Hardesty, B. (1981) Phosphorylation of glycogen synthase and of the beta subunit of eukaryotic initiation factor two by a common protein kinase. *J Biol Chem* 256:8871-4.

Desagher, S., Osen-Sand, A., Montessuit, S., Magnenat, E., Vilbois, F., Hochmann, A., Journot, L., Antonsson, B. and Martinou, J. C. (2001) Phosphorylation of bid by casein kinases I and II regulates its cleavage by caspase 8. *Mol Cell* 8:601-11.

Di Maira, G., Brustolon, F., Pinna, L. A. and Ruzzene, M. (2009) Dephosphorylation and inactivation of AktfPKB is counteracted by protein kinase CK2 in HEK 293T cells. *Cell Mol Life Sci* 66:3363-73.

Di Maira, G., Salvi, M, M., Arrigoni, G., Marin, O., Sarno, S., Brustolon, F., Pinna, L. A. and Ruzzene, M. (2005) Protein kinase CK2 phosphorylates and upregulates Akt/PKB. *Cell Death Differ* 12:668-77.

Dominguez, I., Sonenshein, G. E. and Seldin, D. C. (2009) Protein kinase CK2 in health and disease: CK2 and its role in Wnt and NF-kappaB signaling: linking development and cancer. *Cell Mol Life Sci* 66:1850-7.

Druker, B. J. (2009) Perspectives on the development of imatinib and the future of cancer research. *Nat Med* 15:1149-52.

Eglen, R. M. and Reisine, T. (2009) The current status of drug discovery against the human kinome. *Assay Drug Dev Technol* 7:22-43.

Escalier, D., Silvius, D. and Xu, X. (2003) Spermatogenesis of mice lacking CK2alpha': failure of germ cell survival and characteristic modifications of the spermatid nucleus. *Mol Reprod Dev* 66:190-201.

Farah, M., Parhar, K., Moussavi, M., Eivemark, S, and Salh, B. (2003) 5,6-Dichloro-ribifuranosylbenzimidazole- and apigenin-induced sensitization of colon cancer cells to TNF-alpha-mediated apoptosis. *Am J Physiol Gastrointest Liver Physiol* 285:G919-28.

Faust, M. and Montenarh, M. (2000) Subcellular localization of protein kinase CK2. A key to its function? *Cell Tissue Res* 301:329-40.

Faust, R. A., Niehans, G., Gapany, M., Hoistad, D., Knapp, D., Cherwitz, D., Davis, A., Adams, G. L. and Ahmed, K. (1999) Subcellular immunolocalization of protein kinase CK2 in normal and carcinoma cells. *Int J Biochem Cell Biol* 31:941-9.

Filhol, O. and Cochet, C. (2009) Protein kinase CK2 in health and disease: Cellular functions of protein kinase CK2: a dynamic affair. *Cell Mol Life Sci* 66:1830-9.

Fischer, E. H. (1993) Protein Phosphorylation and Cellular Regulation II (Nobel Lecture). *Angew Chem, Int Ed Engl* 32:1130-7.

Fu, L. and Lee, C. C. (2003) The circadian clock: pacemaker and tumour suppressor. *Nat Rev Cancer* 3:350-61.

Glover, C. V. (1998) On the physiological role of casein kinase II in *Saccharomyces cerevisiae*. *Prog Nucleic Acid Res Mol Biol* 59:95-133.

Graham, K. C. and Litchfield, D. W. (2000) The regulatory beta subunit of protein kinase CK2 mediates formation of tetrameric CK2 complexes. *J Biol Chem* 275:5003-10.

Graziani, Y., Erikson, E. and Erikson, R. L. (1983) Characterization of the Rous sarcoma virus transforming gene product. *J Biol Chem* 258:6344-51.

Guerra, B. (2006) Protein kinase CK2 subunits are positive regulators of AKT kinase. *Int J Oncol* 28:685-93.

Guerra, B. and Issinger, O.-G. (1999) Protein kinase CK2 and its role in cellular proliferation, development and pathology. *Electrophoresis* 20:391-408.

Guerra, B. and Issinger, O.-G. (2008) Protein kinase CK2 in human diseases. *Curr Med Chem* 15:1870-86.

Hanahan, D. and Weinberg, R. A. (2000) The hallmarks of cancer. *Cell* 100:57-70.

Harvey, E. J., Li, N. and Ramji, D. P. (2007) Critical role for casein kinase 2 and phosphoinositide-3-kinase in the interferon-gamma-induced expression of monocyte chemoattractant protein-1 and other key genes implicated in atherosclerosis. *Arterioseler Thromb Vase Biol* 27:806-12.

Hastie, C. J., McLauchlan, H. J. and Cohen, P. (2006) Assay of protein kinases using radiolabeled ATP: a protocol. *Nat Protoc* 1:968-71.

Hidaka, H., Inagaki, M., Kawamoto, S, and Sasaki, Y. (1984) Isoquinolinesulfonamides, novel and potent inhibitors of cyclic nucleotide dependent protein kinase and protein kinase C. *Biochemistry* 23:5036-41.

Homma, M. K. and Homma, Y. (2008) Cell cycle and activation of CK2. *Mol Cell Biochem* 316:49-55.

Hora, R., Bridges, D. J., Craig, A. and Sharma, A. (2009) Erythrocytic casein kinase II regulates cytoadherence of *Plasmodium falciparum*-infected red blood cells. *J Biol Chem* 284:6260-9.

Horoszewicz, J. S., Leong, S. S., Chu, T. M., Wajsman, Z. L., Friedman, M., Papsidero, L., Kim, U., Chai, L. S., Kakati, S., Arya, S. K. and Sandberg, A. A. (1980) The LNCaP cell line-a new model for studies on human prostatic carcinoma. *Prog Clin Biol Res* 37:115-32.

Hung, M.-S., Xu, Z., Lin, Y.-C., Mao, J.-H., Yang, C.-T., Chang, P.-J., Jablons, D. M. and You, L. (2009) Identification of hematein as a novel inhibitor of protein kinase CK2 from a natural product library. *BMC Canc* 9:135.

Jia, Y., Quinn, C. M., Kwak, S, and Talanian, R. V. (2008) Current in vitro kinase assay technologies: the quest for a universal format. *Curr Drug Discov Technol* 5:59-69.

Kelliher, M. A., Seldin, D. C. and Leder, P. (1996) Tal-1 induces T cell acute lymphoblastic leukemia accelerated by casein kinase II alpha. *EMBO J.* 15:5160-6.

Kennedy, E. and Smith, S. (1954) The isolation of radioactive phosphoserine from phosphoprotein of the Ehrlich ascites tumor. *J Biol Chem* 207:153-63.

Kim, J. S., Eom, J. I., Cheong, J.-W., Choi, A. J., Lee, J. K., Yang, W. I. and Min, Y. H. (2007) Protein kinase CK2alpha as an unfavorable prognostic marker and novel therapeutic target in acute myeloid leukemia. *Clin Cancer Res* 13:1019-28.

Klumpp, S, and Krieglstein, J. (2005) Reversible phosphorylation of histidine residues in vertebrate proteins. *Biochim Biophys Acta* 1754:291-5.

Knight, Z. A. and Shokat, K. M. (2005) Features of selective kinase inhibitors. Chem Biol 12:621-37.

Kramerov, A. A., Saghizadeh, M., Caballero, S., Shaw, L. C., Li Calzi, S., Bretner, M., Montenarh, M., Pinna, L. A., Grant, M. B. and Ljubimov, A. V. (2008) Inhibition of protein kinase CK2 suppresses angiogenesis and hematopoietic stem cell recruitment to retinal neovascularization sites. *Mol Cell Biochem* 316:177-86.

Krebs, E. G. (1993) Protein Phosphorylation and Cellular Regulation I (Nobel Lecture). *Angew Chem, Int Ed Engl* 32:1122-9.

Krebs, E. G. and Fischer, E. (1956) The phosphorylase b to a converting enzyme of rabbit skeletal muscle. *Biochim Biophys Acta* 20:150-7.

Kuckländer, U. and Töberich, H. (1982) Zur Umsetzung von 2-(Aminomethylen)cyclohexanon-Derivaten with Dichlorchinonen. *Chem. Ber* 116:152-8.

Kuenzel, E. A., Mulligan, J. A., Sommercorn, J. and Krebs, E. G. (1987) Substrate specificity determinants for casein kinase II as deduced from studies with synthetic peptides. *J Biol Chem* 262:9136-40.

Landesman-Bollag, E., Channavajhala, P. L., Cardiff, R. D. and Seldin, D. C. (1998) p53 deficiency and misexpression of protein kinase CK2alpha collaborate in the development of thymic lymphomas in mice. *Oncogene* 16:2965-74.

Landesman-Bollag, E., Romieu-Mourez, R., Song, D. H., Sonenshein, G. E., Cardiff, R. D. and Seldin, D. C. (2001a) Protein kinase CK2 in mammary gland tumorigenesis. *Oncogene* 20:3247-57.

Landesman-Bollag, E., Song, D. H., Romieu-Mourez, R., Sussman, D. J., Cardiff, R., Sonenshein, G. and Seldin, D. C. (2001b) Protein kinase CK2: signaling and tumorigenesis in the mammary gland. *Mol Cell Biochem* 227:153-65.

Lane, D. P. (1992) Cancer. p53, guardian of the genome. *Nature* 358:15-6.

Laramas, M., Pasquier, D., Filhol, O., Ringeisen, F., Descotes, J.-L. and Cochet, C. (2007) Nuclear localization of protein kinase CK2 catalytic subunit (CK2alpha) is associated with poor prognostic factors in human prostate cancer. *Eur J Cancer* 43:928-34.

Laudet, B., Barette, C., Dulery, V., Renaudet, O., Dumy, P., Metz, A., Prudent, R., Deshiere, A., Dideberg, O., Filhol, O. and Cochet, C. (2007) Structure-based design of small peptide inhibitors of protein kinase CK2 subunit interaction. *Biochem J* 408:363-73.

Laudet, B., Moucadel, V., Prudent, R., Filhol, O., Wong, Y.-S., Royer, D. and Cochet, C. (2008) Identification of chemical inhibitors of protein-kinase CK2 subunit interaction. *Mol Cell Biochem* 316:63-9.

Li, C., Liu, X., Lin, X. and Chen, X. (2009) Structure-activity relationship of 7 flavonoids on recombinant human protein kinase CK2 holoenzyme. *J Cent S Univ Med Sci* 34:20-6.

Li, P.-F., Li, J., Müller, E.-C., Otto, A., Dietz, R. and von Harsdorf, R. (2002) Phosphorylation by protein kinase CK2: a signaling switch for the caspase-inhibiting protein ARC. *Mol Cell* 10:247-58.

Lin, J., Kilman, V. L., Keegan, K., Paddock, B., Emery-Le, M., Rosbash, M. and Allada, R. (2002) A role for casein kinase 2alpha in the *Drosophila* circadian clock. *Nature* 420:816-20.

Lipinski, C. A., Lombardo, F., Dominy, B. and Feeney, P. (2001) Experimental and computational approaches to estimate solubility and permeability in drug discovery and development settings. *Adv Drug Del Rev* 46:3-26.

Litchfield, D. W. (2003) Protein kinase CK2: structure, regulation and role in cellular decisions of life and death. *Biochem J* 369:1-15.

Litchfield, D. W., Bose, D., Canton, D. A., Saulnier, R. B., Vilk, G. and Zhang, C. (2001) Functional specialization of CK2 isoforms and characterization of isoform-specific binding partners. *Mol Cell Biochem* 227:21-9.

Llobet, D., Eritja, N., Encinas, M., Llecha, N., Yeramian, A., Pallares, J., Sorolla, A., Gonzalez-Tallada, F. J., Matias-Guiu, X. and Dolcet, X. (2008) CK2 controls TRAIL and Fas sensitivity by regulating FLIP levels in endometrial carcinoma cells. *Oncogene* 27:2513-24.

Lorenz, P., Pepperkok, R. and Pyerin, W. (1994) Requirement of casein kinase 2 for entry into and progression through early phases of the cell cycle. *Cell Mol Biol Res* 40:519-27.

Lou, D. Y., Dominguez, I., Toselli, P., Landesman-Bollag, E., O'Brien, C. and Seldin, D. C. (2008) The alpha catalytic subunit of protein kinase CK2 is required for mouse embryonic development. *Mol Cell Biol* 28:131-9.

Lozeman, F. J., Litchfield, D. W., Piening, C., Takio, K., Walsh, K. A. and Krebs, E. G. (1990) Isolation and characterization of human cDNA clones encoding the alpha and the alpha' subunits of casein kinase II. *Biochemistry* 29:8436-47.

Ma, H., Deacon, S, and Horiuchi, K. (2008) The challenge of selecting protein kinase assays for lead discovery optimization. *Expert Opin Drug Discov* 3:607-21.

Maier, B., Wendt, S., Vanselow, J. T., Wallach, T., Reischl, S., Oehmke, S., Schlosser, A. and Kramer, A. (2009) A large-scale functional RNAi screen reveals a role for CK2 in the mammalian circadian clock. *Genes Dev* 23:708-18.

Manning, G., Whyte, D. B., Martinez, R., Hunter, T. and Sudarsanam, S. (2002) The protein kinase complement of the human genome. *Science* 298:1912-34.

Mantovani, A., Allavena, P., Sica, A. and Balkwill, F. (2008) Cancer-related inflammation. *Nature* 454:436-44.

McDonnell, M. A., Abedin, M. J., Melendez, M., Platikanova, T. N., Ecklund, J. R., Ahmed, K. and Kelekar, A. (2008) Phosphorylation of murine caspase-9 by the protein kinase casein kinase 2 regulates its cleavage by caspase-8. *J Biol Chem* 283:20149-58.

Medina-Palazon, C., Gruffat, H., Mure, F., Filhol, O., Vingt-deux-Didier, V., Drobecq, H., Cochet, C., Sergeant, N., Sergeant, A. and Manet, E. (2007) Protein kinase CK2 phosphorylation of EB2 regulates its function in the production of Epstein-Barr virus infectious viral particles. *J Virol* 81:11850-60.

Meggio, F., Boldyreff, B., Marin, O., Pinna, L. A. and Issinger, O.-G. (1992) Role of the beta subunit of casein kinase-2 on the stability and specificity of the recombinant reconstituted holoenzyme. *Eur J Biochem* 204:293-7.

Meggio, F. and Pinna, L. A. (2003) One-thousand-and-one substrates of protein kinase CK2? *FASEB J* 17:349-68.

Meggio, F., Shugar, D. and Pinna, L. A. (1990) Ribofuranosyl-benzimidazole derivatives as inhibitors of casein kinase-2 and casein kinase-1. *Eur J Biochem* 187:89-94.

Montenarh, M. (1997) Das Wachstumssuppressorprotein p53, seine zellulären Partner und das Prostatakarzinom. *Aktuel Urol* 28:371-6.

Mottet, D., Ruys, S., Demazy, C., Raes, M. and Michiels, C. (2005) Role for casein kinase 2 in the regulation of HIF-1 activity. *Int J Cancer* 117:764-74.

Münstermann, U., Fritz, G., Seitz, G., Lu, Y. P., Schneider, H. R. and Issinger, O. G. (1990) Casein kinase II is elevated in solid human tumours and rapidly proliferating non-neoplastic tissue. *Eur J Biochem* 189:251-7.

Nie, Z., Perretta, C., Erickson, P., Margosiak, S., Lu, J., Averill, A., Almassy, R. and Chu, S, (2008) Structure-based design and synthesis of novel macrocyclic pyrazolo[1,5-a][1,3,5]triazine compounds as potent inhibitors of protein kinase CK2 and their anticancer activities. *Bioorg Med Chem Lett* 18:619-23.

Niefind, K., Guerra, B., Ermakova, I. and Issinger, O.-G. (2001) Crystal structure of human protein kinase CK2: insights into basic properties of the CK2 holoenzyme. *EMBO J.* 20:5320-31.

Niefind, K. and Issinger, O.-G. (2005) Primary and secondary interactions between CK2alpha and CK2beta lead to ring-like structures in the crystals of the CK2 holoenzyme. *Mol Cell Biochem* 274:3-14.

Niefind, K., Pütter, M., Guerra, B., Issinger, O.-G. and Schomburg, D. (1999) GTP plus water mimic ATP in the active site of protein kinase CK2. *Nat Struct Biol* 6:1100-3.

ole-MoiYoi, O. K. (1995) Casein kinase II in theileriosis. *Science* 267:834-6.

Olsen, B. B., Bjørling-Poulsen, M. and Guerra, B. (2007) Emodin negatively affects the phosphoinositide 3-kinase/AKT signalling pathway: a study on its mechanism of action. *Int J Biochem Cell Biol* 39:227-37.

Olsen, B. B., Boldyreff, B., Niefind, K. and Issinger, O.-G. (2006) Purification and characterization of the CK2alpha'-based holoenzyme, an isozyme of CK2alpha: a comparative analysis. *Protein Expr Purif* 47:651-61.

Olsten, M. E. K. and Litchfield, D. W. (2004) Order or chaos? An evaluation of the regulation of protein kinase CK2. *Biochem Cell Biol* 82:681-93.

Olsten, M. E. K., Weber, J. E. and Litchfield, D. W. (2005) CK2 interacting proteins: emerging paradigms for CK2 regulation? *Mol Cell Biochem* 274:115-24.

Pagano, M. A., Bain, J., J., Kazimierczuk, Z., Sarno, S., Ruzzene, M., Di Maira, G., Elliott, M., Orzeszko, A., Cozza G., Meggio, F. and Pinna, L. A. (2008) The selectivity of inhibitors of protein kinase CK2: an update. *Biochem J* 415:353-65.

Pagano, M. A., Marin, O., Cozza, G., Sarno, S., Meggio, F., Treharne, K. J., Mehta, A. and Pinna, L. A. (2010) Cystic fibrosis transmembrane regulator fragments with the Phe508 deletion exert a dual allosteric control over the master kinase CK2. *Biochem J* 426:19-29.

Pagano, M. A., Meggio, F., Ruzzene, M., Andrzejewska, M., Kazimierczuk, Z. and Pinna, L. A. (2004) 2-Dimethylamino-4,5,6,7-tetrabromo-1H-benzimidazole: a novel powerful and selective inhibitor of protein kinase CK2. *Biochem Biophys Res Commun* 321:1040-4.

Pagano, M. A., Poletto, G., Di Maira, G., Cozza, G., Ruzzene, M., Sarno, S., Bain, J., Elliott, M., Moro, S., Zagotto, G., Meggio, F. and Pinna, L. A. (2007) Tetrabromocinnamic acid (TBCA) and related compounds represent a new class of specific protein kinase CK2 inhibitors. *Chem Bio Chem* 8:129-39.

Pallares, J., Llobet, D., Santacana, M., Eritja, N., Velasco, A., Cuevas, D., Lopez, S., Palomar-Asenjo, V., Yeramian, A., Dolcet, X. and Matias-Guiu, X. (2009) CK2beta is expressed in endometrial carcinoma and has a role in apoptosis resistance and cell proliferation. *Am J Pathol* 174:287-96.

Perea, S. E., Reyes, O., Baladron, I., Perera, Y., Farina, H., Gil, J., Rodriguez, A., Bacardi, D., Marcelo, J. L., Cosine, K., Cruz, M., Valenzuela, C., López-Saura, P. A., Puchades, Y., Serrano, J. M., Mendoza, O., Castellanos, L., Sanchez, A., Betancourt, L., Besada, V., Silva, R., López, E., Falcán, V., Hernández, I., Solares, M., Santana, A., Díaz, A., Ramos, T., López, C., Ariosa, J., González, L. J., Garay, H., Gómez, D., Gómez, R., Alonso, D. F., Sigman, H., Herrera, L. and Acevedo, B. (2008) CIGB-300, a novel proapoptotic peptide that impairs the CK2 phosphorylation and exhibits anticancer properties both in vitro and in vivo. *Mol Cell Biochem* 316:163-7.

Perea, S. E., Reyes, O., Puchades, Y., Mendoza, O., Vispo, N. S., Torrens, I., Santos, A., Silva, R., Acevedo, B., López, E., Falcán, V. and Alonso, D. F. (2004) Antitumor effect of a novel proapoptotic peptide that impairs the phosphorylation by the protein kinase 2 (casein kinase 2). *Cancer Res* 64:7127-9.

Perera, Y., Farina, H. G., Gil, J., Rodriguez, A., Benavent, F., Castellanos, L., Gómez, R. E., Acevedo, B. E., Alonso, D. F. and Perea, S. E. (2009) Anticancer peptide CIGB-300 binds to nucleophosmin/B23, impairs its CK2-mediated phosphorylation, and leads to apoptosis through its nucleolar disassembly activity. *Mol Cancer Ther* 8:1189-96.

Pinna, L. A. (1990) Casein kinase 2: an 'eminence grise' in cellular regulation? *Biochim Biophys Acta* 1054:267-84.

Pinna, L. A. (1994) A historical view of protein kinase CK2. *Cell Mol Biol Res* 40:383-90.

Pinna, L. A. and Allende, J. E. (2009) Protein kinase CK2 in health and disease: Protein kinase CK2: an ugly duckling in the kinome pond. *Cell Mol Life Sci* 66:1795-9.

Prowald, K., Fischer, H. and Issinger, O. G. (1984) Enhanced casein kinase II activity in human tumour cell cultures. *FEBS Lett* 176:479-83.

Prudent, R., Moucadel, V., Laudet, B., Barette, C., Lafanechere, L., Hasenknopf, B., Li, J., Bareyt, S., Lacôte, E., Thorimbert, S., Malacria, M., Gouzerh, P. and Cochet, C. (2008) Identification of polyoxometalates as nanomolar noncompetitive inhibitors of protein kinase CK2. *Chem Biol* 15:683-92.

Prudent, R., Sautel, C. F. and Cochet, C. (2010) Structure-based discovery of small molecules targeting different surfaces of protein-kinase CK2. *Biochim Biophys Acta* 1804:493-8.

Ravi, R. and Bedi, A. (2004) NF-kappaB in cancer-a friend turned foe. *Drug Resist Updat* 7:53-67.

Roig, J., Krehan, A., Colomer, D., Pyerin, W., Itarte, E. and Plana, M. (1999) Multiple forms of protein kinase CK2 present in leukemic cells: in vitro study of its origin by proteolysis. *Mol Cell Biochem* 191:229-34.

Ruzzene, M., Penzo, D. and Pinna, L. A. (2002) Protein kinase CK2 inhibitor 4,5,6,7-tetrabromobenzotriazole (TBB) induces apoptosis and caspase-dependent degradation of haematopoietic lineage cell-specific protein 1 (HS1) in Jurkat cells. *Biochem J* 364:41-7.

Ruzzene, M. and Pinna, L. A. (2010) Addiction to protein kinase CK2: A common denominator of diverse cancer cells? *Biochim Biophys Acta* 1804:499-504.

Ryu, M. Y., Kim, D. W., Arima, K., Mouradian, M. M., Kim, S. U. and Lee, G. (2008) Localization of CKII beta subunits in Lewy bodies of Parkinson's disease. *J Neurol Sci* 266:9-12.

Sale, E. M. and Sale, G. J. (2008) Protein kinase B: signalling roles and therapeutic targeting. *Cell Mol Life Sci* 65:113-27.

Salomoni, P. and Pandolfi, P. P. (2002) The role of PML in tumor suppression. *Cell* 108:165-70.

Salvi, M., Sarno, S., Cesaro, L., Nakamura, H. and Pinna, L. A. (2009) Extraordinary pleiotropy of protein kinase CK2 revealed by weblogo phosphoproteome analysis. *Biochim Biophys Acta* 1793:847-59.

Salvi, M., Sarno, S., Marin, O., Meggio, F., Itarte, E. and Pinna, L. A. (2006) Discrimination between the activity of protein kinase CK2 holoenzyme and its catalytic subunits. *FEBS Lett* 580:3948-52.

Sarno, S., De Moliner, E., Ruzzene, M., Pagano, M. A., Battistutta, R., Bain, J., Fabbro, D., Schoepfer, J., Elliott, M., Furet, P., Meggio, F., Zanotti, G. and Pinna, L. A. (2003) Biochemical and three-dimensional-structural study of the specific inhibition of protein kinase CK2 by [5-oxo-5,6-dihydroindolo-(1,2-a)quinazolin-7-yl]acetic acid (IQA). *Biochem J* 374:639-46.

Sarno, S., Reddy, H., Meggio, F., Ruzzene, M., Davies, S. P., Donella-Deana, A., Shugar, D. and Pinna, L. A. (2001) Selectivity of 4,5,6,7-tetrabromobenzotriazole, an ATP site-directed inhibitor of protein kinase CK2 ('casein kinase-2'). *FEBS Lett* 496:44-8.

Sarno, S., Ruzzene, M., Frascella, P., Pagano, M. A., Meggio, F., Zambon, A., Mazzorana, M., Di Maira, G., Lucchini, V. and Pinna, L. A. (2005) Development and exploitation of CK2 inhibitors. *Mol Cell Biochem* 274:69-76.

Sato, S., Fujita, N. and Tsuruo, T. (2000) Modulation of Akt kinase activity by binding to Hsp90. *Proc Natl Acad Sci USA* 97:10832-7.

Scaglioni, P. P., Yung, T. M., Choi, S. C., Baldini, C., Konstantinidou, G. and Pandolfi, P. P. (2008) CK2 mediates phosphorylation and ubiquitin-mediated degradation of the PML tumor suppressor. *Mol Cell Biochem* 316:149-54.

Schneider, C. C., Hessenauer, A., Götz, C. and Montenarh, M. (2009) DMAT, an inhibitor of protein kinase CK2 induces reactive oxygen species and DNA double strand breaks. *Oncol Rep* 21:1593-7.

Schneider, C. C., Hessenauer, A., Montenarh, M. and Götz, C. (2010) $p^{53}$ is dispensable for the induction of apoptosis after inhibition of protein kinase CK2. *Prostate* 70:126-34.

Seldin, D. C., Landesman-Bollag, E., Farago, M., Currier, N., Lou, D. and Dominguez, I. (2005) CK2 as a positive regulator of Wnt signalling and tumourigenesis. *Mol Cell Biochem* 274:63-7.

Seldin, D. C. and Leder, P. (1995) Casein kinase II alpha transgene-induced murine lymphoma: relation to theileriosis in cattle. *Science* 267:894-7.

Seldin, D. C., Lou, D. Y., Toselli, P., Landesman-Bollag, E. and Dominguez, I. (2008) Gene targeting of CK2 catalytic subunits. *Mol Cell Biochem* 316:141-7.

Shi, X., Potvin, B., Huang, T., Hilgard, P., Spray, D. C., Suadicani, S. O., Wolkoff, A. W., Stanley, P. and Stockert, R. J. (2001) A novel casein kinase 2 alpha-subunit regulates membrane protein traffic in the human hepatoma cell line HuH-7. *J Biol Chem* 276:2075-82.

Shimoyama, Y., Sakamoto, R., Akaboshi, T., Tanaka, M. and Ohtsuki, K. (2001) Characterization of secretory type IIA phospholipase A2 (sPLA2-IIA) as a glycyrrhizin (GL)-binding protein and the GL-induced inhibition of the CK-II-mediated stimulation of sPLA2-IIA activity in vitro. *Biol Pharm Bull* 24:1004-8.

Shin, S., Lee, Y., Kim, W., Ko, H., Choi, H. and Kim, K. (2005) Caspase-2 primes cancer cells for TRAIL-mediated apoptosis by processing procaspase-8. *EMBO J.* 24:3532-42.

Siemer, S., Stalter, G., Ziegler, M. and Issinger, O. (1996) Charakterisierung der Proteinkinase CK2 in menschlichen Nierentumoren. *Aktuel Urol* 27:1-5.

Singh, N. N. and Ramji, D. P. (2008) Protein kinase CK2, an important regulator of the inflammatory response? *J Mol Med* 86:887-97.

Slaton, J. W., Unger, G., Sloper, D., Davis, A. and Ahmed, K. (2004) Induction of apoptosis by antisense CK2 in human prostate cancer xenograft model. *Mol Cancer Res* 2:712-21.

Stalter, G., Siemer, S., Becht, E., Ziegler, M., Remberger, K. and Issinger, O.-G. (1994) Asymmetric expression of protein kinase CK2 subunits in human kidney tumors. *Biochem Biophys Res Res Commun* 202:141-7.

Sugano, S., Andronis, C., Ong, M. S., Green, R. M. and Tobin, E. M. (1999) The protein kinase CK2 is involved in regulation of circadian rhythms in *Arabidopsis*. *Proc Natl Acad Sci USA* 96:12362-6.

Suzuki, Y., Cluzeau, J., Hara, T., Hirasawa, A., Tsujimoto, G., Oishi, S., Ohno, H. and Fujii, N. (2008) Structure-activity relationships of pyrazine-based CK2 inhibitors: synthesis and evaluation of 2,6-disubstituted pyrazines and 4,6-disubstituted pyrimidines. *Arch Pharm* (Weinheim) 341:554-61.

Tawfic, S., Yu, S., Wang, H., Faust, R., Davis, A. and Ahmed, K. (2001) Protein kinase CK2 signal in neoplasia. *Histol Histopathol* 16:573-82.

Thornburg, W. and Lindell, T. J. (1977) Purification of rat liver nuclear protein kinase NII. *J Biol Chem* 252:6660-5.

Tiganis, T., House, C. M. and Kemp, B. E. (1993) Casein kinase II beta-subunit inhibits the activity of the catalytic alpha-subunit in the absence of salt. *Biochim Biophys Acta* 1203:282-9.

Torres, J. and Pulido, R. (2001) The tumor suppressor PTEN is phosphorylated by the protein kinase CK2 at its C terminus. Implications for PTEN stability to proteasome-mediated degradation. *Biol Chem* 276:993-8.

Trembley, J. H., Wang, G., G., Unger, G., Slaton, J. and Ahmed, K. (2009) Protein kinase CK2 in health and disease: CK2: a key player in cancer biology. *Cell Mol Life Sci* 66:1858-67.

Tsuchiya, Y., Akashi, M., Matsuda, M., Goto, K., Miyata, Y., Node, K. and Nishida, E. (2009) Involvement of the protein kinase CK2 in the regulation of mammalian circadian rhythms. *Sci Signal* 2:ra26.

Ubersax, J. A. and Ferrell, J. E. (2007) Mechanisms of specificity in protein phosphorylation. *Nat Rev Mol Cell Biol* 8:530-41.

Unger, G., Davis, A. T., Slaton, J. W. and Ahmed, K. (2004) Protein kinase CK2 as regulator of cell survival: implications for cancer therapy. *Curr Cancer Drug Tar* 4:77-84.

Valero, E., De Bonis, S., Filhol, O., Wade, R. H., Langowski, J., Chambaz, E. M. and Cochet, C. (1995) Quaternary structure of casein kinase 2. Characterization of multiple oligomeric states and relation with its catalytic activity. *J Biol Chem* 270:8345-52.

Vilk, G., Weber, J. E., Turowec, J. P., Duncan, J. S., Wu, C., Derksen, D. R., Zien, P., Sarno, S., Donella-Deana, A., Lajoie, G., Pinna, L. A., Li, S. S. C. and Litchfield, D. W. (2008) Protein kinase CK2 catalyzes tyrosine phosphorylation in mammalian cells. *Cell Signal* 20:1942-51.

Villar-Palasi, C. and Kumon, A. (1981) Purification and properties of dog cardiac troponin T kinase. *J Biol Chem* 256:7409-15.

Walsh, D. A., Perkins, J. P. and Krebs, E. G. (1968) An adenosine 3',5'-monophosphate-dependant protein kinase from rabbit skeletal muscle. *J Biol Chem* 243:3763-5.

Wang, G., Unger, G., Ahmad, K., Slaton, J. W. and Ahmed, K. (2005) Downregulation of CK2 induces apoptosis in cancer cells-a potential approach to cancer therapy. *Mol Cell Biochem* 274:77-84.

Wang, L., Lin, L. and Ye, B. (2006) Electrochemical studies of the interaction of the anticancer herbal drug emodin with DNA. *J Pharm Biomed Anal* 42:625-9.

Wang, S, and Jones, K. A. (2006) CK2 controls the recruitment of Wnt regulators to target genes in vivo. *Curr Biol* 16:2239-44.

Willert, K., Brink, M., Wodarz, A., Varmus, H. and Nusse, R. (1997) Casein kinase 2 associates with and phosphorylates dishevelled. *EMBO J.* 16:3089-96.

Xu, X., Landesman-Bollag, E., Channavajhala, P. L. and Seldin, D. C. (1999a) Murine protein kinase CK2: gene and oncogene. *Mol Cell Biochem* 191:65-74.

Xu, X., Toselli, P. A., Russell, L. D. and Seldin, D. C. (1999b) Globozoospermia in mice lacking the casein kinase II alpha' catalytic subunit. *Nat Genet.* 23:118-21.

Yamada, M., Katsuma, S., Adachi, T., Hirasawa, A., Shiojima, S., Kadowaki, T., Okuno, Y., Koshimizu, T.-a., Fujii, S., Sekiya, Y., Miyamoto, Y., Tamura, M., Yumura, W., Nihei, H., Kobayashi, M. and Tsujimoto, G. (2005) Inhibition of protein kinase CK2 prevents the progression of glomerulonephritis. *Proc Natl Acad Sci USA* 102:7736-41.

Yan, J. X., Packer, N. H., Gooley, A. A. and Williams, K. L. (1998) Protein phosphorylation: technologies for the identification of phosphoamino acids. *J Chromatogr A* 808:23-41.

Yang, Y., Cheng, P. and Liu, Y. (2002) Regulation of the *Neurospora* circadian clock by casein kinase II. *Genes Dev* 16:994-1006.

Yenice, S., Davis, A. T., Goueli, S. A., Akdas, A., Limas, C. and Ahmed, K. (1994) Nuclear casein kinase 2 (CK-2) activity in human normal, benign hyperplastic, and cancerous prostate. *Prostate* 24:11-6.

Yim, H., Lee, Y. H., Lee, C. H. and Lee, S. K. (1999) Emodin, an anthraquinone derivative isolated from the rhizomes of *Rheum palmatum*, selectively inhibits the activity of casein kinase II as a competitive inhibitor. *Planta Med* 65:9-13.

Zandomeni, R., Zandomeni, M. C., Shugar, D. and Weinmann, R. (1986) Casein kinase type II is involved in the inhibition by 5,6-dichloro-1-beta-D-ribofuranosylbenzimidazole of specific RNA polymerase II transcription. *J Biol Chem* 261:3414-9.

Zien, P., Duncan, J. S., Skierski, J., Bretner, M., Litchfield, D. W. and Shugar, D. (2005) Tetrabromobenzotriazole (TBBt) and tetrabromobenzimidazole (TBBz) as selective inhibitors of protein kinase CK2: evaluation of their effects on cells and different molecular forms of human CK2. *Biochim Biophys Acta* 1754:271-80.

The invention claimed is:

1. A pharmaceutical composition, characterized in that it comprises, as an active ingredient, at least one compound with general formula I:

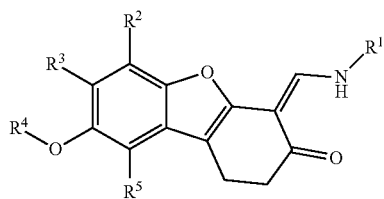

wherein R1 is a substituted or unsubstituted aryl group or a substituted or unsubstituted alkyl group containing 1 to 16 C atoms, preferably a halogen, alkoxy and/or alkyl-substituted aryl group; R2, R3 and R5 are independently F, Cl, Br, I, H, a hydroxyl group or an alkoxy group containing 1 to 4 C atoms; and R4 is H, an alkyl or acyl group containing 1 to 16 C atoms, preferably $(C_nH_{2n+1})$—CO, with n=1, 2, 3, 4, 5, 6, 7 or 8, pharmaceutically acceptable additives and/or auxiliary substances, and at least one further compound with an antineoplastic effect.

2. The composition according to claim 1, wherein R1 is a para-substituted aryl group; R2 and R3 are independently F, Cl or H; R4 is H or $CH_3CO$; and R5 is H.

3. The composition according to claim 2, wherein R1=4-$CH_3OC_6H_4$, 4-$CH_3C_6H_4$ or 4-$FC_6H_6$.

4. The composition according to claim 1, wherein R1=4-$CH_3C_6H_4$; R2 and R3=Cl; and R4 and R5=H.

* * * * *